US 7,485,723 B2

(12) United States Patent
Gupta et al.

(10) Patent No.: US 7,485,723 B2
(45) Date of Patent: *Feb. 3, 2009

(54) PROCESS FOR MAKING TRISARYL TRIAZINE UV ABSORBERS USING LEWIS ACIDS AND REACTION PROMOTERS

(75) Inventors: Ram B. Gupta, Stamford, CT (US); Dennis J Jakiela, Orange, CT (US); Sampath Venimadhavan, Stamford, CT (US); Russell C Cappadona, Norwalk, CT (US); Venkatrao K. Pai, Stamford, CT (US)

(73) Assignee: Cytec Technology Corp., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/531,932

(22) Filed: Sep. 14, 2006

(65) Prior Publication Data

US 2007/0015920 A1 Jan. 18, 2007

Related U.S. Application Data

(60) Continuation of application No. 11/089,289, filed on Mar. 24, 2005, now abandoned, which is a continuation of application No. 10/835,731, filed on Apr. 30, 2004, now Pat. No. 6,900,314, which is a continuation of application No. 09/779,597, filed on Feb. 9, 2001, now Pat. No. 6,730,785, which is a division of application No. 09/442,000, filed on Nov. 17, 1999, now Pat. No. 6,486,316.

(60) Provisional application No. 60/108,786, filed on Nov. 17, 1998.

(51) Int. Cl.
*C07D 251/24* (2006.01)
(52) U.S. Cl. ..................... 544/216; 544/217
(58) Field of Classification Search ................ 544/216, 544/217
See application file for complete search history.

(56) References Cited

U.S. PATENT DOCUMENTS

| 1,551,095 | A * | 8/1925 | Fritsche et al. | 544/217 |
| 3,118,887 | A * | 1/1964 | Pinto et al. | 544/216 |
| 6,242,598 | B1 * | 6/2001 | Stevenson et al. | 544/216 |
| 6,486,316 | B1 * | 11/2002 | Gupta et al. | 544/216 |
| 6,900,314 | B2 * | 5/2005 | Gupta et al. | 544/216 |

* cited by examiner

*Primary Examiner*—Venkataraman Balasubramanian
(74) *Attorney, Agent, or Firm*—Elizabeth A. Galletta; Fran S. Wasserman

(57) ABSTRACT

It has been now surprisingly discovered after extensive research that 2-halo-4,6-bisaryl-1,3,5-triazine can be prepared with unprecedented selectivity, efficiency, mild conditions, and in high yield by the reaction of cyanuric halide with aromatics in the presence of at least one Lewis acid and at least one reaction promoter. This reaction is also unprecedently general as a variety of aromatics can be used to produce a wide selection of 2-halo-4,6-bisaryl-1,3,5-triazines. The novel approach includes the use of the reaction promoters in combination with at least one Lewis acid under certain reaction conditions to promote the formation of 2-halo-4,6-bisaryl-1,3,5-triazine compounds from cyanuric halide. Preferably, the Lewis acids and reaction promoters are combined to form a complex 2-Halo-4,6-bisaryl-1,3,5-triazines are key intermediates for making 2-(2-oxyaryl)-4,6-bisaryl-1,3,5-triazine class of UV absorbers.

21 Claims, No Drawings

PROCESS FOR MAKING TRISARYL TRIAZINE UV ABSORBERS USING LEWIS ACIDS AND REACTION PROMOTERS

CROSS REFERENCE OF RELATED APPLICATIONS

This application is a continuation of U.S. patent application Ser. No. 11/089,289, filed Mar. 24, 2005, now abandoned which in turn is a continuation of U.S. patent application Ser. No. 10/835,731, filed Apr. 30, 2004, now U.S. Pat. No. 6,900,314, which is a continuation of U.S. patent application Ser. No. 09/779,597, filed Feb. 9, 2001, now U.S. Pat. No. 6,730,785; which is a divisional application of U.S. patent application Ser. No. 09/442,000, filed Nov. 17, 1999, now U.S. Pat. No. 6,486,316 B1; which claims benefit of U.S. Provisional Application No. 60/108,786, filed Nov. 17, 1998, the content of which is expressly incorporated herein.

FIELD OF THE INVENTION

This invention relates to a novel, highly efficient and general process for making 2-(2-oxyaryl)-4,6-bisaryl-1,3,5-triazines class of trisaryl-1,3,5-triazine UV absorbers and their precursors, 2-halo-4,6-bisaryl-1,3,5-triazines, from cyanuric halide. More specifically, the invention relates to a novel process for the synthesis of triazine compounds in the presence of a reaction facilitator comprising at least one Lewis acid and at least one reaction promoter. The process includes the reaction of a cyanuric halide with substituted or unsubstituted aromatic compounds to produce 2-halo-4,6-bisaryl-1,3,5-triazine compounds. This process produces halo-bisaryl-1,3,5-triazine compounds in higher yields than are possible using present methods. The triazine compounds that are produced are precursors of triazine UV absorbers which are used to stabilize organic materials against damage by light, heat, oxygen, or other environmental forces. The process of producing such UV absorbers can be carried out step-wise or continuously in an one-pot reaction process.

BACKGROUND OF HE INVENTION

Triazine UV absorbers are an important class of organic compounds which have a wide variety of applications. One of the most important areas of applications is to protect and stabilize organic materials such as plastics, polymers, coating materials, and photographic recording material against damage by light, heat, oxygen, or environmental forces. Other areas of applications include cosmetics, fibers, dyes, etc.

Triazine derived UV absorbers are a class of compounds that typically include at least one 2-oxyaryl substituent on the 1,3,5-triazine ring. Triazine based UV absorber compounds having aromatic substituents at the 2-, 4-, and 6-positions of the 1,3,5-triazine ring and having at least one of the aromatic rings substituted at the ortho position with a hydroxyl group or blocked hydroxyl group are generally preferred compounds.

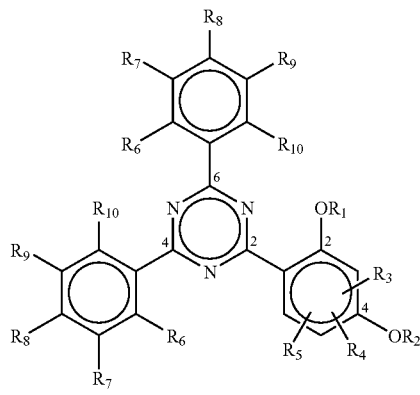

$R_1$ = H or a blocking group
2-(2-oxyaryl)-4,6-bisaryl-1,3,5-triazine UV absorbers In general this class of triazine UV absorber compounds is well known in the art. Disclosures of a number of such trisaryl-1,3,5-triazines can be found in the following U.S. patents, all of which are incorporated by reference as fully set forth herein: U.S. Pat. Nos. 3,118,887; 3,242,175; 3,244,708; 3,249,608; 3,268,474; 3,423,360; 3,444,164; 3,843,371; 4,619,956; 4,740,542; 4,775,707; 4,826,978; 4,831,068; 4,962,142; 5,030,731; 5,059,647; 5,071,981; 5,084,570; 5,106,891; 5,185,445; 5,189,084; 5,198,498; 5,288,778; 5,298,067; 5,300,414; 5,323,868; 5,354,794; 5,364,749; 5,369,140; 5,410,048; 5,412,008; 5,420,008; 5,420,204; 5,461,151; 5,476,937; 5,478,935; 5,489,503; 5,543,518; 5,538,840; 5,545,836; 5,563,224; 5,575,958; 5,591,850; 5,597,854; 5,612,084; 5,637,706; 5,648,488; 5,672,704; 5,675,004; 5,681,955; 5,686,233; 5,705,643; 5,726,309; 5,726,310; 5,741,905; and 5,760,111.

A preferred class of trisaryltriazine UV absorbers (UVAs) are based on 2-(2,4-dihydroxyaryl)-4,6-bisaryl-1,3,5-triazines, i.e., compounds with two non-phenolic aromatic groups and one phenolic aromatic group advantageously derived from resorcinol. The 4-hydroxyl group of the parent compounds, 2-(2,4-dihydroxyaryl)-4,6-bisaryl-1,3,5-triazines, are generally functionalized to make 2-(2-hydroxy-4-alkoxyaryl)-4,6-bisaryl-1,3,5-triazine compounds for end use.

A number of commercial products exist in which the para-hydroxyl group of the phenolic ring is functionalized and the non-phenolic aromatic rings are either unsubstituted phenyl (e.g., linuvin® 1577) or m-xylyl (e.g. Cyasorb® UV-1164, Cyasorb® UV-1164L, Tinuvin® 400, and CCL-1545). These UV absorbers are preferred because they exhibit high inherent light stability and permanence compared to other classes of UV absorbers such as benzotriazole and benzophenone compounds.

There are several processes known in the literature for the preparation of triazine based UV absorbers. (See, H. Brunetti and C. E. Luethi, *Helvetica Chimica Acta*, 1972, 55, 1566-1595, S. Tanimoto et al, *Senryo to Yakahin*, 1995, 40(120), 325-339).

A majority of the approaches consist of three stages. The first stage, the synthesis of the key intermediate, 2-chloro-4,6-bisaryl-1,3,5-triazine, from commercially available materials can involve single or multi-step processes. Thereafter in the second stage, 2-chloro-4,6-bisaryl-1,3,5-triazine is subsequently arylated with 1,3-dihydroxybenzene (resorcinol) or a substituted 1,3-dihydroxybenzene in the presence of a Lewis acid to form the parent compound 2-(2,4-dihydroxyaryl)-4,6-bisaryl-1,3,5-triazine. The parent compound 2-(2,4-dihydroxyaryl)-4,6-bisaryl-1,3,5-triazine, as mentioned above, may be further functionalized, e.g., alkylated, to make a final product 2-(2-hydroxy-4-alkoxyaryl)-4,6-bisaryl-1,3,5-triazine.

There have been several approaches reported in the literature on the synthesis of the key intermediate 2-chloro-4,6-bisaryl-1,3,5-triazine. Many of these approaches utilize cyanuric chloride, a readily available and inexpensive starting material. For example, cyanuric chloride is allowed to react with aromatics (ArH, such as m-xylene) in the presence of aluminum chloride (Friedel-Crafts reaction) to form 2-chloro-4,6-bisaryl-1,3,5-triazine, which is allowed to react in a subsequent step with resorcinol to form 2-(2,4-dihydroxyphenyl)-4,6-bisaryl-1,3,5-triazine (See, U.S. Pat. No. 3,244,708). There are several limitations to this process, viz., the reaction of cyanuric chloride with aromatics is not selective and leads to a mixture of mono-, bis-, and tris-arylated products including unreacted cyanuric chloride (See, Scheme 1). The desired product, 2-chloro-4,6-bisaryl-1,3,5-triazine, must be isolated by crystallization or other purification methods before further reaction.

Scheme 1

Step 1:

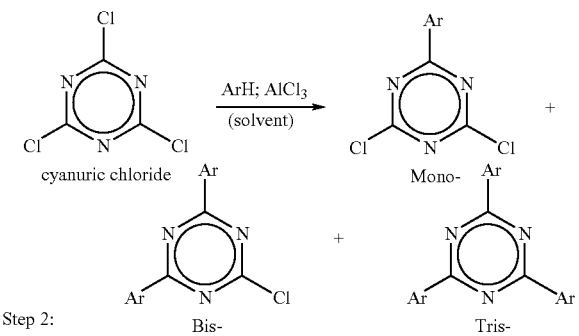

Step 2:

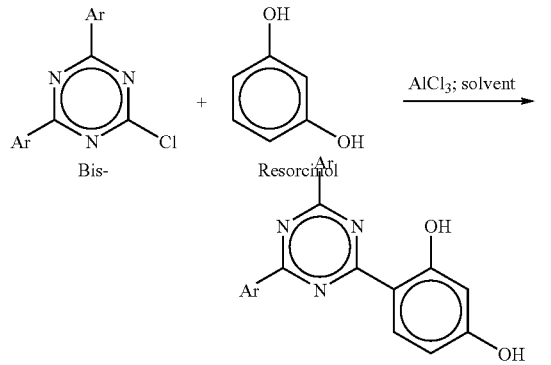

2-(2,4-dihydroxyphenyl)-4,6-bisaryl-1,3,5-triazines

Another major drawback of the above mentioned process is that the reaction of cyanuric chloride with aromatics is not generally applicable to all aromatics. It is well known in the literature that the process provides a useful yield of the desired intermediate, 2-chloro-4,6-bisaryl-1,3,5-triazine, only when m-xylene is the aromatic reagent (GB 884802). With other aromatics, an inseparable mixture of mono-, bis-, and trisaryl products are formed with no selectivity for the desired 2-chloro-4,6-bisaryl-1,3,5-triazine (See, H. Brunetti and C. E. Luethi, *Helvetica Chimica Acta*, 1972, 55, 1575; and S. Tanimoto and M Yamagata, *Senryo to Takahin*, 1995, 40(12), 325-339). U.S. Pat. No. 5,726,310 describes the synthesis of m-xylene based products 2-chloro-4,6-bis(2,4-dimethylphenyl)-1,3,5-triazine is first synthesized and without isolation allowed to react with resorcinol in a one-pot, two-step process to produce 2-(2,4-dihydroxyphenyl)-4,6-bis(2,4-dimethylphenyl)-1,3,5-triazine, which is subsequently purified by crystallization. A one pot process for preparing asymmetric tris-aryl-1,3,5-triazines from cyanuric chloride as well as from mono-aryl-dichloro triazines was earlier described in U.S. Pat. No. 3,268,474.

Several approaches were developed in an attempt to solve the above mentioned problems related to the formation of the key intermediate 2-chloro-4,6-bisaryl-1,3,5-triazine from cyanuric chloride. For example, cyanuric chloride is allowed to react with an aryl magnesium halide (Grignard reagent), to prepare 2-chloro-4,6-bisaryl-1,3,5-triazine (See, Ostrogovich, Chemiker-Zeitung, 1912, 78, 738; Von R. Hirt, H. Nidecker and R. Berchtold, *Helvetica Chimica Acta*, 1950, 33, 365; U.S. Pat. No. 4,092,466). This intermediate after isolation can be subsequently reacted in the second step with resorcinol to make a 2-(2,4-dihydroxyphenyl)-4,6-bisaryl-1,3,5-triazine (See, Scheme 2). This approach does not selectively synthesize 2-chloro-4,6-bisaryl-1,3,5-triazine; the mono- and tris-arylated products are formed in significant amounts (See, H. Brunetti and C. E. Luethi, *Helvetica Chimica Acta*, 1972, 55, 1575). Modifications with better results have been reported (See, U.S. Pat. No. 5,438,138). Additionally, the modified process is not suitable for industrial scale production and is not economically attractive.

Scheme 2

Step 1:

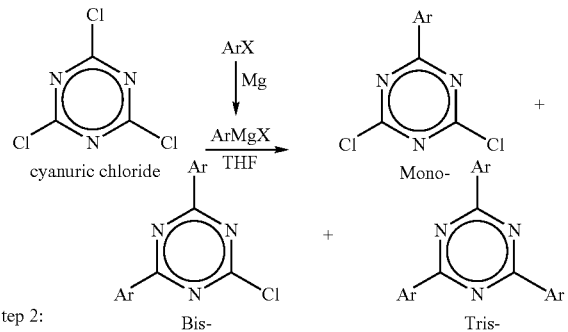

Step 2:

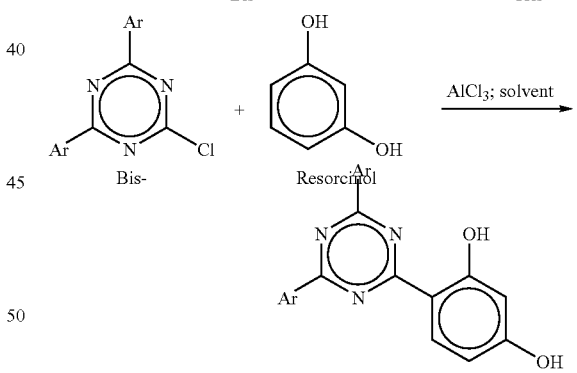

2-(2,4-dihydroxyphenyl)-4,6-bisaryl-1,3,5-triazines

Alternate approaches were developed to solve the selectivity problem when synthesizing 2-chloro-4,6-bisaryl-1,3,5-triazine using either a Friedel-Crafts reaction or Grignard reagents, however, all solutions required additional synthetic steps. One approach, is outlined in Scheme 3. In the first step, cyanuric chloride is allowed to react with 1 equivalent of an aliphatic alcohol to make in high selectivity a monoalkoxy-bischlorotriazine. In the second step, monoalkoxy-bischlorotriazine was allowed to react with aromatics in the presence of aluminum chloride to prepare intermediates monoalkoxy/hydroxy-bisaryltriazines. These intermediates were then converted to 2-chloro-4,6-bisaryl-1,3,5-triazines in the third step by reaction with thionyl chloride or PCl$_5$. In the fourth step, 2-chloro-4,6-bisaryl-1,3,5-triazines were allowed to react with resorcinol to synthesize 2-(2,4-dihydroxyphenyl)-4,6-bisaryl-1,3,5-triazines. In the above process, the desired product was formed with high selectivity. However, the two additional Recent improvements are disclosed in European patent application 0,779,280 A1 and Japanese patent application 09-059263.

Other approaches do not utilize cyanuric chloride as a starting material. For example, the synthesis of 2-chloro-4,6-

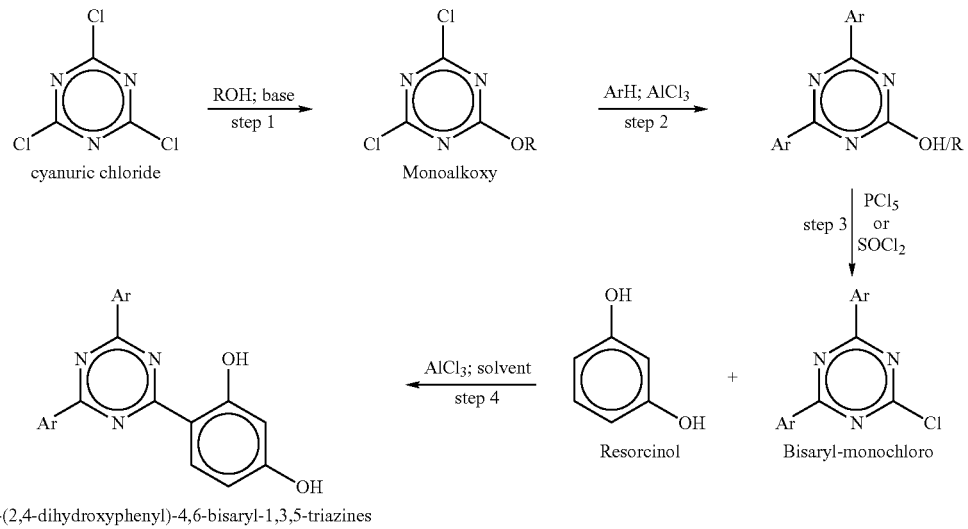

steps required made the process less attractive economically as an industrial process.

A similar approach is outlined in Scheme 4 (See, U.S. Pat. Nos. 5,106,972 and 5,084,570). The main difference is that cyanuric chloride was first allowed to react with 1 equivalent of alkanethiol, instead of an alcohol. As with the process summarized in Scheme 3, additional steps were required, making the process neither efficient nor economically feasible.

bisaryl-1,3,5-triazine as disclosed in EP 0497734 A1 and as outlined in Scheme 5. In this process benzamidine hydrochloride is first allow to react with a chloroformate and the resulting product is then dimerized. The resulting 2-hydroxy-4,6-bisaryl-1,3,5-triazine is converted to 2-chloro-4,6-bisaryl-1,3,5-triazine by treatment with thionyl chloride, which is subsequently allowed to react with resorcinol to synthesize 2-(2,4-dihydroxyphenyl)-4,6-bisaryl-1,3,5-triazine, as shown in Scheme 5

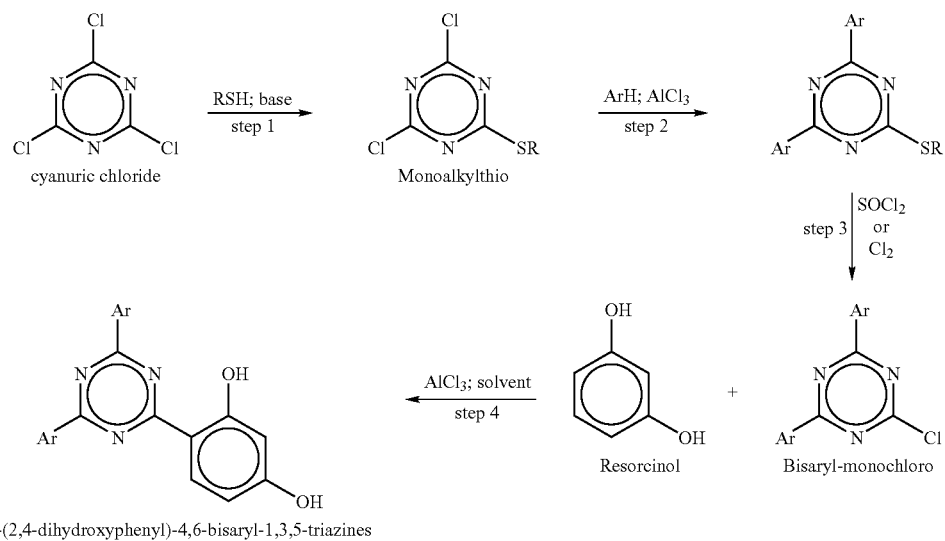

Scheme 5

Synthesis of Benzamidines:

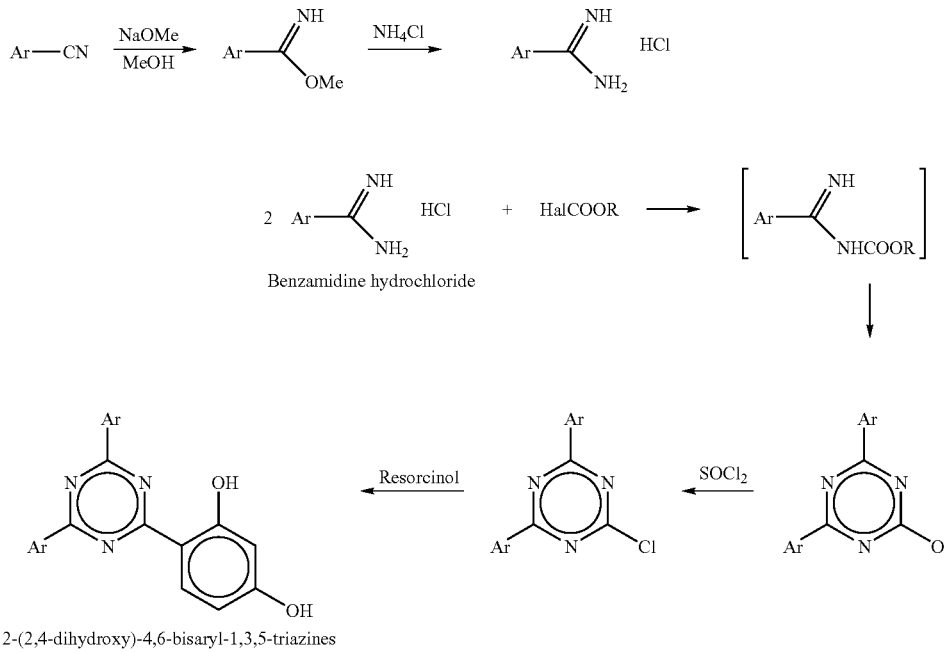

2-(2,4-dihydroxy)-4,6-bisaryl-1,3,5-triazines

An alternate approach for the preparation of 2-chloro-4,6-bisaryl-1,3,5-triazines is based on the reaction of aryl nitriles with phosgene in the presence of HCl in a sealed tube (S. Yanagida, H. Hayama, M. Yokoe, and S. Komori, *J. Org. Chem.*, 1969, 34, 4125. Another approach is the reaction of N,N-dimethylbenzamide with phosphoryl chloride complex which is then allowed to react with N-cyanobenzamidine to form 2-chloro-4,6-bisaryl-1,3,5-triazine (R. L. N. Harris, *Synthesis*, 1990, 841). Yet another approach involves the reaction of polychloroazalkenes, obtained from the high temperature of chlorination of amines, with amidines to form 2-chloro-4,6-bisaryl-1,3,5-triazines (H. G. Schmelzer, E. Degener and H. Holtschmidt, *Angew. Chem. Internat. Ed.*, 1966, 5, 960; DE 1178437). None of these approaches are economically attractive, and thus are not commercially feasible.

Finally, there are at least the approaches which do not require the intermediacy of 2-chloro-4,6-bisaryl-1,3,5-triazine for the preparation of the parent compound, 2-(2,4-dihydroxyaryl)-4,6-bisaryl-1,3,5-triazine. These approaches utilize benzonitriles or benzamidines as starting materials (See U.S. Pat. Nos. 5,705,643 and 5,478,935; WO 96/28431). The benzamidines are condensed with 2,4-dihydroxybenzaldehyde followed by aromatization (Scheme 6) or condensed with phenyl/alkyl 2,4-dihydroxybenzoates (Scheme 7) or 2-aryl-1,3-benzoxazine-4-ones (Scheme 8) to form 2-(2,4,-dihydroxyaryl)-4,6-bisaryl-1,3,5-triazine. These approaches have the drawback that the starting materials are expensive and may require additional steps to prepare. Moreover, overall yields are not satisfactory and the processes are not economically attractive.

Based on Benzamidine reactions with 2,4-dihydroxybenzaldehyde:

Scheme 6

Synthesis of Benzamidines:

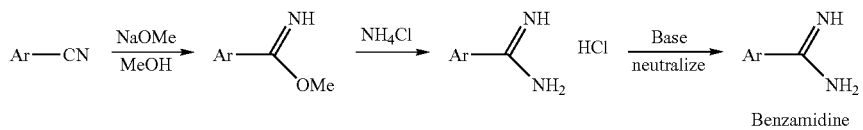

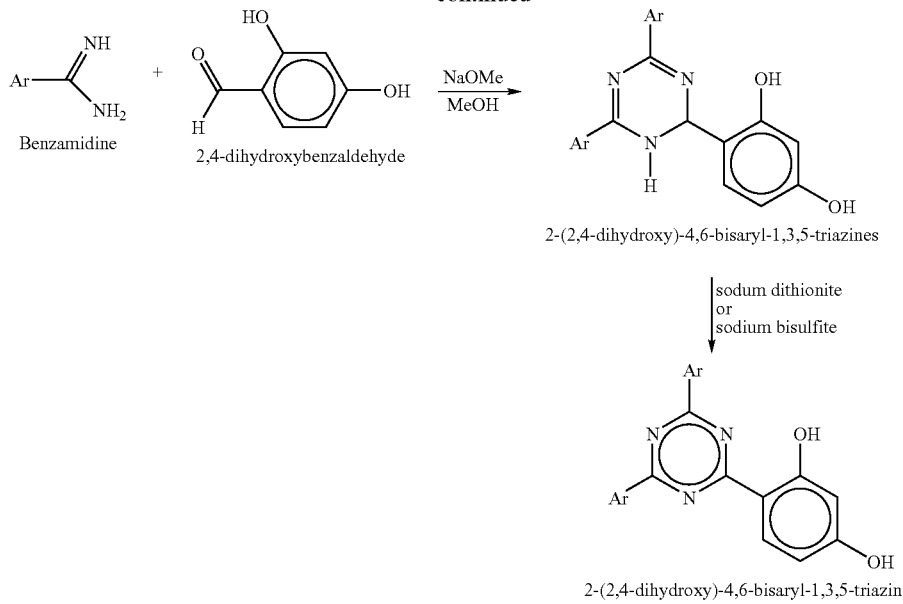
2-(2,4-dihydroxy)-4,6-bisaryl-1,3,5-triazines
2-(2,4-dihydroxy)-4,6-bisaryl-1,3,5-triazines
Based on Benzamidine reactions with Phenyl 2,4-dihydroxybenzoate
Scheme 7
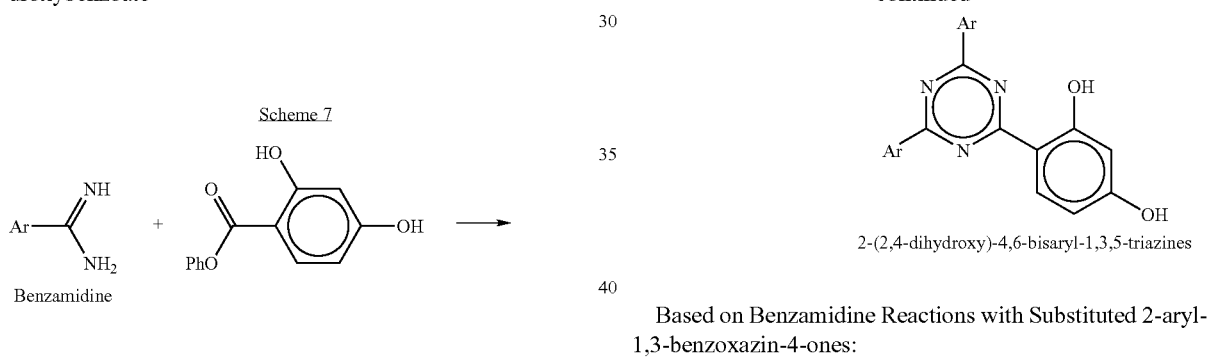
2-(2,4-dihydroxy)-4,6-bisaryl-1,3,5-triazines
Based on Benzamidine Reactions with Substituted 2-aryl-1,3-benzoxazin-4-ones:
Scheme 8
Synthesis of Benzamidines:
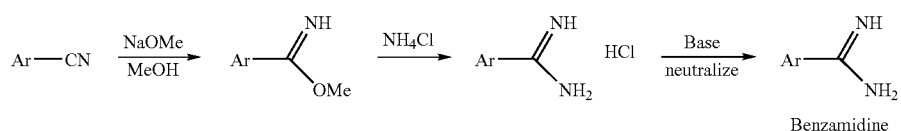
Synthesis of 2-aryl-1,3-benzoxazin-4-ones:
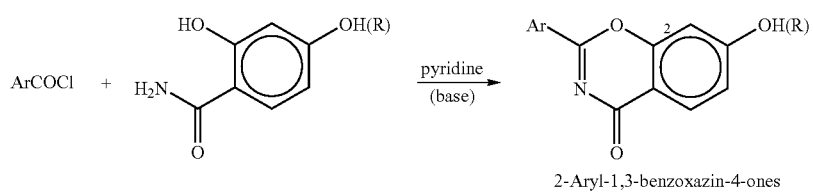
2-Aryl-1,3-benzoxazin-4-ones -continued

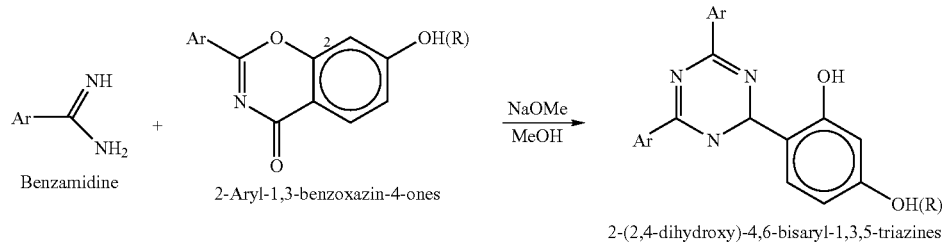

Benzamidine + 2-Aryl-1,3-benzoxazin-4-ones →(NaOMe/MeOH)→ 2-(2,4-dihydroxy)-4,6-bisaryl-1,3,5-triazines In summary, although direct Lewis acid catalyzed bisarylation of cyanuric chloride to form the desired 2-chloro-4,6-bisaryl-1,3,5-triazine intermediate is the most economically attractive approach, this process has found only limited use due to the following problems:

1. Poor selectivity: Almost total lack of selectivity for bisarylation (with the exception of m-xylene where some selectivity is observed). Mono- and tris-arylated triazines are the major by-products.
2. Poor reactivity: Typical reaction conditions require high temperatures, long reaction times, and variable temperatures during the course of reaction. Aromatics with electron-withdrawing groups (such as chlorobenzene) fail to react beyond mono-substitution even at elevated temperatures and long reaction times.
3. Safety hazards: Temperature and addition rate must be carefully monitored to avoid an uncontrollable exothermic which may result in safety hazards.
4. Poor process conditions: The reaction slurry is either thick and difficult to stir or solid thereby making stirring impossible. The process requires various reaction temperatures and addition of reactants in portions over several hours.
5. Isolation problem/poor isolated yield: Separation and purification of the desired product is difficult and isolated yields are generally poor and commercially unacceptable
6. Not a general process: The reaction cannot be used with different aromatics other than m-xylene.

Thus, there remains a need for improved methods for synthesizing triazine UV absorbers.

SUMMARY OF THE INVENTION

It has been now surprisingly discovered after extensive research that 2-halo-4,6-bisaryl-1,3,5-triazine can be prepared with unprecedented selectivity, efficiency, mild conditions, and in high yield by the reaction of cyanuric halide with aromatics in the presence of a reaction facilitator comprising at least one Lewis acid and at least one reaction promoter. This reaction is also unprecedently general as a variety of aromatics can be used to produce a wide selection of 2-halo-4,6-bisaryl-1,3,5-triazines. The novel approach includes the use of the reaction promoter in combination with at least one Lewis acid under certain reaction conditions to promote the formation of 2-halo-4,6-bisaryl-1,3,5-triazine compounds from cyanuric halide. Preferably, the Lewis acids and reaction promoters are combined to form a reaction facilitator in the form of a complex.

The present invention specifically relates to a process for the synthesis of a triazine compound by reacting a cyanuric halide of Formula V:

Formula V

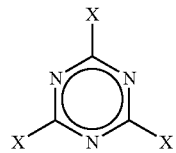

with at least one substituted or unsubstituted aromatic compound such as a compound of Formula II:

Formula II

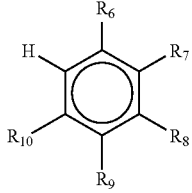

wherein $R_6$, $R_7$, $R_8$, $R_9$, and $R_{10}$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms including substituted or unsubstituted biphenylene, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, and optionally with either of $R_6$ and $R_7$, $R_7$ and $R_8$, $R_8$ and $R_9$, or $R_9$ and $R_{10}$, taken together being a part of a saturated or unsaturated fused carbocyclic ring optionally containing O, N, or S atoms in the ring, with the reaction being conducted in the presence of at least one reaction facilitator comprising at least one Lewis acid and at least one reaction promoter, optionally in an inert solvent, for a sufficient time at a suitable temperature and pressure to produce a triazine compound of Formula III:

Formula III

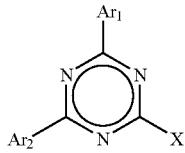

wherein X is a halogen and $Ar_1$ and $Ar_2$ are the same or different and each may be the radical of a compound of Formula II:

Radical of Formula II

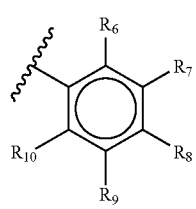

In a further embodiment, the triazine compound of Formula III is further reacted with a compound of Formula IV:

Formula IV

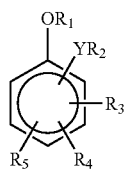

wherein $R_1$, $R_2$, $R_3$, $R_4$, and $R_5$ are the same or different and each is hydrogen, halogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 25 carbon atoms, cycloacyl of 5 to 24 carbon atoms, aralkyl of 7 to 24 carbon atoms, aracyl of 6 to 24 carbons atoms, substituted or unsubstituted biphenylene, substituted or unsubstituted naphthalene, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, optionally with either of $R_3$ and $R_4$, or $R_4$ and $R_5$, taken together being a part of a saturated or unsaturated fused carbocyclic ring optionally containing O, N, or S atoms in the ring, and Y is a direct bond, O, NR", or SR"wherein R"is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, optionally in the presence of an additional Lewis acid, additional reaction promoter, or additional reaction facilitator; for a sufficient time at a suitable temperature and pressure, optionally in the presence of an inert solvent, to produce a compound of Formula I:

Formula I

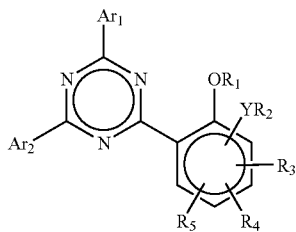

The reaction to form the compound of Formula III and the reaction to from the compound of Formula I can be carried out without isolating the compound of Formula III.

Another embodiment relates to a process for synthesizing a triazine compound of Formula I:

Formula I

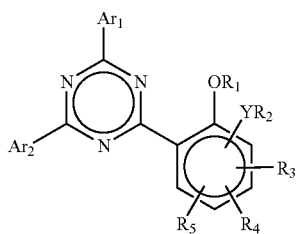

wherein $Ar_1$ and $Ar_2$ are the same or different, and each independently is a radical of a compound of Formula II:

Formula II

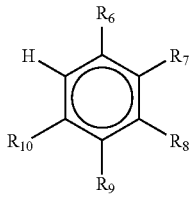

wherein $R_6$, $R_7$, $R_8$, $R_9$, and $R_{10}$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms including substituted or unsubstituted biphenylene, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, and optionally with either of $R_6$ and $R_7$, $R_7$ and $R_8$, $R_8$ and $R_9$, or $R_9$ and $R_{10}$, taken together being a part of a saturated or unsaturated fused carbocyclic ring optionally containing O, N, or S atoms in the ring, which comprises:

simultaneously reacting in the presence of a reaction facilitator comprising at least one Lewis acid and at least one reaction promoter, sufficient amounts of a cyanuric halide of Formula V:

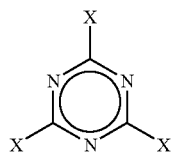

Formula V where each X is independently a halide such as fluorine, chlorine, bromine or iodine, with a compound of Formula IV:

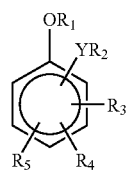

Formula IV wherein $R_1$, $R_2$, $R_3$, $R_4$, and $R_5$ are the same or different and each is hydrogen, halogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 25 carbon atoms, cycloacyl of 5 to 24 carbon atoms, aralkyl of 7 to 24 carbon atoms, aracyl of 6 to 24 carbons atoms, substituted or unsubstituted biphenylene, substituted or unsubstituted naphthalene, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, optionally with either of $R_3$ and $R_4$, or $R_4$ and $R_5$, taken together being a part of a saturated or unsaturated fused carbocyclic ring optionally containing O, N or S atoms in the ring, and Y is a direct bond, O, NR", or SR" wherein R" is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, and a compound of formula I:

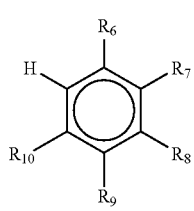

Formula II for a sufficient time, at a suitable temperature and pressure to form the compound of Formula I.

Another embodiment relates to a process for synthesizing a triazine compound of Formula I:

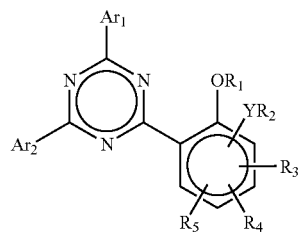

Formula I wherein $Ar_1$, and $Ar_2$ are the same or different, and each independently is a radical of a compound of Formula II:

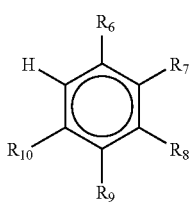

Formula II wherein $R_6$, $R_7$, $R_8$, $R_9$, and $R_{10}$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms including substituted or unsubstituted biphenylene, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, and optionally with either of $R_6$ and $R_7$, $R_7$ and $R_8$, $R_8$ and $R_9$, $R_9$ and $R_{10}$, taken together being a part of a saturated or unsaturated fused carbocyclic ring optionally containing O, N, or S atoms in the ring, which comprises:

reacting in the presence of a reaction facilitator comprising at least one Lewis acid and at least one reaction promoter, sufficient amounts of a compound of Formula III:

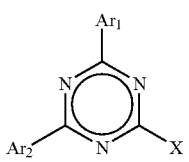

Formula III wherein X is independently a halide such as fluorine, chorine, bromine or iodine and $Ar_1$ and $Ar_2$ are the same or different and each is a radical of a compound of Formula II; with a compound of Formula IV:

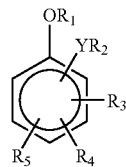

Formula IV

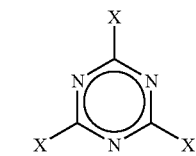

Formula V wherein $R_1$, $R_2$, $R_3$, $R_4$, and $R_5$ are the same or different and each is hydrogen, halogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 25 carbon atoms, cycloacyl of 5 to 24 carbon atoms, aralkyl of 7 to 24 carbon atoms, aracyl of 6 to 24 carbons atoms, substituted or unsubstituted biphenylene, substituted or unsubstituted naphthalene, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, optionally with either of $R_3$ and $R_4$, or $R_4$ and $R_5$, taken together being a part of a saturated or unsaturated fused carbocyclic ring optionally containing O, N, or S atoms in the ring, and Y is a direct bond, O, NR", or SR" wherein R" is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, for a sufficient time, at a suitable temperature and pressure to form the compound of Formula I.

DETAILED DESCRIPTION OF THE INVENTION

The present inventors have found that by using a combination comprising of at least one Lewis acid and at least one reaction promoter; preferably combined to form a reaction facilitator, the reaction of a cyanuric halide with substituted or unsubstituted aromatic compounds can prepare triazine derived 2-halo-4,6-bisaryl-1,3,5-triazine compounds in higher yield with higher selectivity, at a lower reaction temperature, and/or within shorter reaction times than previously known.

Even more surprising is the fact that the reaction facilitator has been used with excellent results. This approach is in stark contrast to the state of the prior art where the use of anhydrous Lewis acids alone has always been advocated for this reaction step. It has also been discovered that 2-halo-4,6-bisaryl-1,3,5-triazines of this invention can be further reacted, without isolation, with a variety of phenolic derivatives to form 2-(2-oxyaryl)-4,6-bisaryl-1,3,5-triazine. Furthermore, the reaction can be applied to a variety of aromatic compounds. The key reasons for the increase in selectivity and reactivity has been shown to be the use of the reaction promoter.

As used herein, the cyanuric halide is a compound of the Formula V:

where each X is independently a halide such as fluorine, chlorine, bromine, or iodine.

The term aromatic compound is to include compounds of the Formula II:

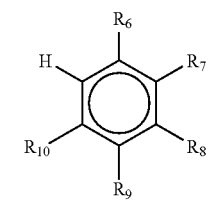

Formula II wherein $R_6$, $R_7$, $R_8$, $R_9$, and $R_{10}$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms including substituted or unsubstituted biphenylene, OR, NRR', CONRR', OCOR, CN, SR, $SO_2R$, $SO_3H$, $SO_3M$, wherein M is an alkali metal, R and R' are the same or, different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, and optionally with either of $R_6$ and $R_7$, $R_7$ and $R_8$, $R_8$ and $R_9$, or $R_9$ and $R_{10}$, taken together being a part of a saturated or unsaturated fused carbocyclic ring optionally containing O, N, or S atoms in the ring.

Preferred aromatic compounds include benzene, toluene, ethylbenzene, m-xylene, o-xylene, p-xylene, chlorobenzene, dichlorobenzene, mesitylene, isobutylbenzene, isopropylbenzene, m-diisopropyl benzene, tetralin, biphenyl, naphthalene, acetophenone, benzophenone, acetanilide, anisole, thioanisole, resorcinol, bishexyloxy resorcinol, bisoctyloxy resorcinol, m-hexyloxy phenol, m-octyloxy phenol, or a mixture thereof.

The term "phenolic compound" is to include compounds of the formula IV:

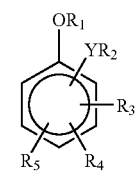

Formula IV wherein $R_1$, $R_2$, $R_3$, $R_4$, and $R_5$ are the same or different and each is hydrogen, halogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 25 carbon atoms, cycloacyl of 5 to 24 carbon atoms, aralkyl of 7 to 24 carbon atoms, aracyl of 6 to 24 carbons atoms, substituted or unsubstituted biphenylene, substituted or unsubstituted naphthalene, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, optionally with either of $R_3$ and $R_4$, or $R_4$ and $R_5$, taken together being a part of a saturated or unsaturated fused carbocyclic ring optionally containing O, N, or S atoms in the ring, and Y is a direct bond, O, NR", or SR" wherein R" is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms.

Preferred phenolic compounds are substituted or unsubstituted monohydroxybenzene, monalkoxybenzene, dihydroxybenzene, dialkoxybenzene, hydroxyalkoxybenzene, trihydroxybenzene, trialkoxybenzene, hydroxybisalkoxybenzene, and bishydroxyalkoxybenzene. More preferred phenolic compounds are: resorcinol (1,3-dihydroxybenzene); C-alkylated resorcinols, e.g, 4-hexylhesorcinol; mono-O-alkylated fresorcinols, e.g, 3-methoxyphenol, 3-octyloxyphenol, 3-hexyloxyphenol, etc.; di-O-alkylated resorcinols, e.g., 1,3-dimethoxybenzene, 1,3-dioctylbenzene, 1,3-dihexyloxybenzene; C-alkylated-di-O-alkylated resorcinols, e.g., 4-hexyl-1,3-dimethoxybenzene; other polyhydroxy, polyalkoxy, hydroxy-alkoxy aromatics, e.g., 1,3,5-trihydroxybenzene, 1,3,5-trialkoxybenzene, 1,4-dihydroxybenzene, 1-hydroxy-4-alkoxybenzene, or mixtures thereof.

The term "Lewis acid" is intended to include aluminum halides, alkylaluminum halides, boron halides, tin halides, titanium halides, lead halides, zinc halides, iron halides, gallium halides, arsenic halide, copper halides, cadmium halides, mercury halides, antimony halides, thallium halides, zirconium halides, tungsten halides, molybdenum halides, niobium halides, and the like. Preferred Lewis acids include aluminum trichloride, aluminum tribromide, trimethylaluminum, boron trifluoride, boron trichloride, zinc dichloride, titanium tetrachloride, tin dichloride, tin tetrachloride, ferric chloride, or a mixture thereof.

As used herein the term "reaction promoter" is understood to comprise a compound which is used in combination with the Lewis acid to facilitate the reaction. Thus, triazine compounds are produced at lower reaction temperatures, greater yields, or higher selectivities compared to the use of the Lewis acid alone. Suitable reaction promoters include acids, bases, water, alcohols, aliphatic halides, halide salts, acid halides, halogens, alkenes, alkynes, ester, anhydride, carbonate, urethane, carbonyl, epoxy, ether; acetal compounds, or mixtures thereof.

Suitable alcohol compounds include carbon compounds of $C_1$-$C_{20}$, straight chain or branched, saturated or unsaturated, cyclic or non-cyclic, aromatic or non-aromatic, which has at least one hydroxyl group and which optionally contains at least one halide, thiol, thiol ether, amines, carbonyl, esters, carboxylic acids, amide, etc. Suitably alcohols include methanol, ethanol, propanol, butanol, isobutanol, t-butanol, 1,2-ethanediol, 3-chloro-1-propanol, 2-hydroxy-acetic acid, 1-hydroxyl-3-pentanone, cyclohexanol, cyclohexenol, glycerol, phenol, m-hydroxyl-anisole, p-hydroxyl-benzylamine, benzyl alcohol, etc.

Suitable acid compounds include any inorganic or organic acid that contains at least one acidic proton, which may or may not be dissolved in an aqueous or organic solution. The organic acids include any organic compound that contains at least one acidic functional group including $RCO_2H$, $RSO_3H$, $RSO_2H$, RSH, ROH, $RPO_3H$, $RPO_2H$, wherein R is as defined above. Preferred protic acids include HCl, HBr, HI, $HNO_3$, $HNO_2$, $H_2S$, $H_2SO_4$, $H_3PO_4$, $H_2CO_3$, acetic acid, formic acid, propionic acid, butanoic acid, benzoic acid, phthalic acid, oxalic acid, malonic acid, succinic acid, glutaric acid, adipic acid, methanesulfonic acid, and p-toluenesulfonic acid or mixtures thereof.

Suitable aliphatic halides include $C_1$-$C_{20}$ hydrocarbon compounds, saturated or unsaturated, cyclic or non-cyclic, aromatic or non-aromatic, that are substituted with at least one halide. Optionally, the aliphatic halide may be substituted in one or more positions with an hydroxyl, an ether a polyether, a thiol, a thioether; an amine, such as —NHR, —NR'$_2$, —NRR', a carboxylic acid, an ester, an amide or a carbon structure of $C_1$-$C_{20}$ group which may be saturated or unsaturated and cyclic or non-cyclic, aromatic and which optionally may be substituted with any of the above preceding groups or mixtures thereof.

Specific aliphatic halide compounds that are suitable include carbon tetrachloride, chloroform, methylene chloride, chloromethane, carbon tetrabromide, tert-butylchloride, bromoform, dibromomethane, bromomethane, diiodomethane, iodomethane, dichloroethane, dibromoethane, chloroethanol, bromoethanol, benzyl chloride, benzyl bromide, ethanolamine, chloroacetic acid, bromoacetic acid or mixtures thereof.

The bases that are suitable include inorganic or organic bases dissolved either in water, an organic solvent, or a mixture of solvents. Inorganic bases include LiOH, NaOH, KOH, $Mg(OH)_2$, $Ca(OH)_2$, $Zn(OH)_2$, $Al(OH)_3$, $NH_4OH$, $Li_2CO_3$, $Na_2CO_3$, $K_2CO_3$, $MgCO_3$, $CaCO_3$, $ZnCO_3$, $(Al)_3(CO_3)_2$, $(NH_4)_3CO_3$, $LiNH_2$, $NaNH_2$, $KNH_2$, $Mg(NH_2)_2$, $Ca(NH_2)_2$, $Zn(NH_2)_2$, $Al(NH_2)_3$, or a mixture thereof. Organic bases include hydrocarbon compounds with $C_1$-$C_9$ cyclic or non-cyclic that contain at least one alkoxide, amine, amide, carboxylate, or thiolate and which may be substituted in one or more positions with a halide, an hydroxyl, an ether, a polyether, a thiol, a thioether, an amine, such as —NHR, —NR'$_2$, —NRR', a carboxylic acid, an ester, or an amide. Organic bases include $CH_3O^-$, $CH_3CH_2O^-$, $CH_3CH_2CH_2O^-$, $(CH_3)_2CHO^-$, $((CH_3)_2CH)_2CHO^-$, $CH_3CH_2CH_2CH_2O^-$, $(CH_3)_3CO^-$, $CH_3NH_2$, $CH_3CH_2NH_2$, $CH_3CH_2CH_2NH_2$, $(CH_3)_2CHNH_2$, $((CH_3)_2CH)_2CHNH_2$, $CH_3CH_2CH_2CH_2NH_2$, $(CH_3)_3CNH_2$, $(CH_3)_2NH$, $(CH_3CH_2)_2NH$, $(CH_3CH_2CH_2)_2NH$, $((CH_3)_2CH)_2NH$, $(((CH_3)_2CH)_2CH)_2NH$, $(CH_3CH_2CH_2CH_2)_2NH$, $((CH_3)_3C)_2NH$, $(CH_3)_3N$, $(CH_3CH_2)_3N$, $(CH_3CH_2CH_2)_3N$, $((CH_3)_2CH)_3N$, $(((CH_3)_2CH)_2CH)_3N$, $(CH_3CH_2CH_2CH_2)_3N$, $((CH_3)_3C)_3N$, $CH_3NH^-$, $CH_3CH_2NH^-$, $CH_3CH_2CH_2NH^-$, $(CH_3)_2CHNH^-$, $((CH_3)_2CH)_2CHNH^-$, $CH_3CH_2CH_2CH_2NH^-$, $(CH_3)_3CNH^-$, $(CH_3)_2N^-$, $(CH_3CH_2)_2N^-$, $(CH_3CH_2CH_2)_2N^-$, $((CH_3)_2CH)_2N^-$, $(((CH_3)_2CH)_2CH)_2N^-$, $(CH_3CH_2CH_2CH_2)_2N^-$, $((CH_3)_3C)_2N^-$, pyrriolidine, piperidine, pyrrole, pyridine, aniline, tetramethylenediamine, the corresponding deprotonated amine, and a cation were appropriate. Organic bases also includes salts of deprotonated carboxylic acids such as salts of formate, acetate, propylate, butanoate, benzoate, with Li, Na, K, Mg, Ca, Al, Zn, or any other suitable cation.

Organic base includes mixtures of the aforementioned inorganic and organic bases, or a mixture thereof.

Halogen reaction promoters include fluorine, chlorine, bromine, iodine, or mixed halogens dissolved in either water, an organic solvent, or a mixture of solvents or present as part of an organic or inorganic compound. Halogenated solvents that are suitable include dichloromethane, chloroform, carbon tetrachloride, di-bromomethane, bromoform, iodomethane, diiodomethane, dichloroethane, 1,1,2,2-tetrachloroethane, benzene, toluene, acetone, acetic acid, hexane, or a mixture thereof.

Additional reaction promoters that are suitable include hydrocarbon compounds of Formula VI:

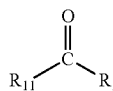

Formula VI wherein $R_{11}$ and $R_{12}$ are either the same or different, may be taken together, hydrogen, hydrocarbon $C_1$-$C_{20}$, saturated or unsaturated, aromatic or non-aromatic cyclic or non-cyclic, hydroxyl, ether amine, substituted amine, carboxylate, ester, amide, and may be substituted at least once with a halide, hydroxyl, amine, amide, thiol, thioether, carboxylate, or a carbon structure of $C_1$-$C_{12}$ group which may be saturated or unsaturated and cyclic or non-cyclic, and which optionally may be substituted with any of the above preceding groups, or mixtures thereof.

Additional compounds of Formula VI include those wherein $R_{11}$ and $R_{12}$ are either the same or different, may be taken together; hydrocarbon $C_1$-$C_{12}$, saturated or unsaturated, cyclic or non-cyclic, hydroxyl, ether, mine, substituted amine, carboxylate, ester, amide, and may be substituted at least once with a halide, hydroxyl, amine, amide, thiol, thioether, carboxylate, or a carbon structure of $C_1$-$C_7$ group which may be saturated or unsaturated and cyclic or non-cyclic, and which optionally may be substituted with any of the above preceding groups, including hydrocarbon compounds acetaldehyde, butyraldehyde, glutaric dialdehyde, crotonaldehyde, benzaldehyde, acetone, methyl vinyl ketone, acetophenone, cyclohexanone, 2-cyclohexen-1-one, methyl acrylate, acetic anhydride, crotonic anhydride, phthalic anhydride, succinic anhydride, maleic anhydride, dimethyl adipate, diethyl phthalate, dimethyl carbonate, ethylene carbonate, diphenyl carbonate, phenyl carbamate, benzyl carbamate, methyl carbamate, urethane, propyl carbamate, or mixtures thereof.

Suitable ether compounds as reaction promoters include hydrocarbon compounds $C_2$-$C_{20}$, saturated or unsaturated, aromatic or non-aromatic, cyclic or non-cyclic, that have at least one C—O—C bond, and optionally are substituted with at least one halide, hydroxyl, amine, thiol, thioether; carboxylic acid, ester, or a carbon structure of $C_1$-$C_{12}$ group which may be saturated or unsaturated and cyclic or non-cyclic, and which optionally may be substituted with any of the above preceding groups or mixtures thereof.

Additional ether compounds are hydrocarbon compounds of $C_2$-$C_{12}$ that have at least one C—O—C bond, saturated or unsaturated, aromatic or non-aromatic, cyclic or non-cyclic, and may be substituted at least once with a halide, hydroxyl, amine, ether, thiol, thioether, carboxylic acid, ester; or a carbon structure of $C_1$-$C_7$ group which may be saturated or unsaturated and cyclic or non-cyclic, and which optionally may be substituted with any of the above preceding groups including hydrocarbon compounds dimethyl ether; isopropyl ether, dipropyl ether; tert-amyl methyl ether; tert-butyl ethyl ether; allyl phenyl ether; allyl propyl ether, 4-methoxyphenyl ether, 3,3-dimethyl oxetane, dioxane, tetrahydropyran, tetrahydro-4H-pyran-4-ol, ethylene oxide, propylene oxide, styrene oxide, glycidol, glycidyl methyl ether glycidyl butyrate, glycidyl methacrylate, 1,2-epoxy-3-phenoxypropane, 1,2-epoxyhexane, 1-chloro-2,3-epoxypropane, diethyl acetal, 2,2-dimethoxypropane, 1,1-dimethoxycyclohexane, 2-hexenal diethyl acetal, 3-chloropropionaldehyde diethyl acetal, benzaldehyde dimethyl acetal, 1,1,3-trimethoxypropane, or a mixture thereof.

Alkene reaction promoters include hydrocarbon compounds $C_2$-$C_{20}$ that include at least one C—C double bond or C—C triple bond, whether the compounds are cyclic, heterocyclic or non-cyclic, and where the compounds are optionally substituted at least once with a halide, hydroxyl, amine, ether; thiol, thioether carboxylic acid, ester; or a carbon structure of $C_1$-$C_{12}$ group which may be saturated or unsaturated and cyclic or non-cyclic and which optionally may be substituted with any of the above preceding groups, or mixtures thereof.

Additional alkene reaction promoters include hydrocarbon compounds of $C_2$-$C_{12}$ with at least one C—C double bond or C—C triple bond, cyclic, heterocyclic or non-cyclic, and may be substituted at least once with a halide, hydroxyl, amine, ether, thiol, thioether; carboxylic acid, ester; or a carbon structure of $C_1$-$C_7$ group which may be saturated or unsaturated and cyclic or non-cyclic, and which optionally may be substituted with any of the above preceding groups including hydrocarbon compounds 2-methylpropene, 1-butene, 2-butene, 2-methyl-2-butene, 1-pentene, 2-methyl-2-pentene, 3-methyl-2-pentene, 2-pentene, 2-methyl-2-pentene, 3-methyl-2-pentene, 4-methyl-2-pentene, 2-methyl-2-pentenoic acid, 3-methyl-1-penten-3-ol, 5-chloro-1-pentene, 4-bromo-2-methyl-2-butene, 1,4-pentadiene, 2,6-heptadienoic acid, hexatriene, cyclohexene, cyclohexadiene, cyclopentadiene, 2-cyclopenten-1-one, 2-methylfuran, styrene, methylstyrene, methyl vinyl ketone, acrylic acid, methyl acrylate, 1-pentyne, 2-pentyne, 2-pentyn-1-ol, 6-chloro-1-hexyne, 1,6-heptadiyne, or mixtures thereof;

Further reaction promoters include compounds of the formula RCOX, RSOX, $RSO_2X$, or RPOX wherein at least one carbon, sulfur, or phosphorus atom is double bonded with at least one oxygen atom or phosphorous halides such as $PX_3$ and $PX_5$ wherein X is at least one halide from the group F, Cl, Br, and I. R is at least one halide or hydrocarbon $C_1$-$C_{20}$ saturated or unsaturated, cyclic or non-cyclic, and may be substituted at least once with a halide, hydroxyl, amine, ether; thiol or mixtures thereof.

Compounds where R includes chloro, bromo, methyl; ethyl, propyl, isopropyl, butyl, phenyl, tolyl, naphthalyl, X includes F, Cl, Br, I, including compounds such as thionyl chloride, thionyl bromide, phosphorus oxybromide, phosphorus oxychloride, phosgene, acetyl chloride, acetyl bromide, benzoyl chloride, benzoyl bromide, toluoyl chloride, toluenesulfonyl chloride, terephthaloyl chloride, terephthaloyl bromide, oxalyl dichloride, oxalyl dibromide, succinyl dichloride, glutaryl dichloride, adipoyl dichloride, pimeloyl dichloride, methanesulfonyl chloride, ethanesulfonyl chloride, propanesulfonyl chloride, isopropylsulfonyl chloride, butanesulfonylchloride, benzenesulfonyl chloride, methyl dichlorophosphite, phosphoric acid halides, $PCl_3$, $PBr_3$, $PCl_5$, $PBr_5$, or mixtures thereof are suitable.

Compounds of the formula $M_aX_b$ are also suitable reaction promoters, wherein the bond dissociation energy of M-X is about less than 145 kcal/mol at 298° Kelvin and where M includes at least one metal or organic cation of the formula $NR_4^+$, $SR_3^+$, or $PR_4^+$ where R includes $C_1$-$C_6$ which may be substituted at least one halide hydroxyl, amine, ether, thiol or mixtures thereof and where X is at least one anion.

Inorganic or organic compounds defined above that are suitable are also soluble in water or organic solvents such as methanol, ethanol, isopropanol, methylene chloride, acetone, diethyl ether, tetrahydrofuran, ethylene glycol, xylene, and chlorobenzene. These compounds include antimony halides, arsenic halides, barium halides, beryllium halides, bismuth halides, boron halides, cadmium halides, calcium halides, cerium halides, cesium halides, cesium tetrachloroaluminates, cobalt halides, copper halides, gold halides, iron halides, lanthanum halides, lithium halides, lithium tetrachloroaluminates, magnesium halides, manganese halides, mercury halides, nickel halides, osmium halides, phosphorus halides, potassium halides, potassium hydrogen fluorides, potassium tetrachloroaluminates, rhodium halides, samarium halides, selenium halides, silver halides, sodium halides, tin halides, lanthanum halides, sodium hydrogen fluorides, sodium tetrachloroaluminates, sodium/potassium tetracloroaurates, sodium/potassium/lithium/zinc/copper tetrafluoroborates, thalium halides, titanium chloride-aluminum chlorides (x:y), titanium halides, yttrium halides, zinc halides, zirconium halides, ammonium halides, tetraalkyl quaternary ammonium halides, aralkyl trialkylquaternary ammonium halides, arayl trialkylammonium halides, alkyl N-alkylimidazolium halides, aralkyl N-alkylimidazolium halides, alkyl N-aralkylimidazolium halides, N-alkylpyridinium halides, N-alkylisoquinolinium halides, N-alkylquinolinium halides, triphenylphosphonium halides, haloalkyl triphenylphosphonium halides, carboxyalkyl triphenylphosphonium halides, carbalkoxyalkyl triphenylphosphonium halides, cycloalkyl triphenylphosphonium halides, alkenyl triphenylphosphonium halides, aralkyltriphenylphosphonium halides, hydroxyaralkyl phosphonium halides, tetraphenylphosphonium halides, trialkylsulphonium halides, including but not limited to, inorganic compounds where M includes $Li^+$, $Na^+$, $K^+$, $Mg^{2+}$, $Ca^{2+}$, $Sr^{2+}$, $Ba^{2+}$, $Ti^{4+}$, $CO^{2+}$, $Ni^{2+}$, $Cu^+$, $Cu^{2+}$, $Sn^{2+}$, $Sn^{4+}$, $Pb^{2+}$, $Pb^{4+}$, $Ce^{3+}$, and $Ce^{4+}$; organic compounds where M includes $^+N(CH_3)_4$, $^+N(CH_2CH_3)_4$, $^+N(CH_2CH_2CH_3)_4$, $^+N(CH_2CH_2CH_2CH_3)_4$, $^+NPh_4$, $^+P(CH_3)_4$, $^+P(CH_2CH_3)_4$, $^+P(CH_2CH_2CH_3)_4$, $^+P(CH_2CH_2CH_2CH_3)_4$, $^+PPh_4$, $^+S(CH_3)_3$, $^+S(CH_2CH_3)_3$, $^+S(CH_2CH_2CH_3)_3$, $^+S(CH_2CH_2CH_2CH_3)_3$, $^+SPh_3$, pyridinium, imidazolium, pyrrolidinium, and pyrrolium, and X includes inorganic X includes $Cl^-$, $Br^-$, $I^-$, $S^{2-}$, $O^{2-}$, $CO_3^{2-}$, $SO_3^{2-}$, $SO_4^{2-}$, $NO_2^-$, $NO_3^-$, $BF_4^-$, $OH^-$, $PO_3^{2-}$, $PO_4^{2-}$, $ClO_4^-$, $MnO_4^-$; organic X includes $HCO_2^-$, $CH_3CO_2^-$, $CH_3^-$, $CH_3CH_2^-$, $Ph^-$, $CH_3O^-$, $CH_3CH_2O^-$, $PhO^-$, $CH_3S^-$, $CH_3CH_2S^-$, $PhS^-$, $CH_3NH^-$, $CH_3CH_2NH^-$, $PhNH^-$ or mixtures thereof.

The reaction promoter may also be water alone or as an aqueous solution or aqueous suspension, that contains other components therein, such as one or more of the promoters mentioned above.

Optionally, a combination of at least one Lewis acid and at least one reaction promoter, i.e. a reaction facilitator; is prepared before being added to the reactants.

The term "solvent" includes hydrocarbon compounds $C_1$-$C_{24}$ saturated or unsaturated, cyclic or non-cyclic, aromatic or non-aromatic, optionally substituted with at least one halide, nitro, or sulfide group. Preferred solvents are hydrocarbons $C_1$-$C_8$, saturated or unsaturated, such as nitroalkanes, heptane, cyclohexane, benzene, nitrobenzene, dinitrobenzene, toluene, xylene, 1,1,2,2-tetrachloroethane, dichloromethane, dichloroethane, ether, dioxane, tetrahydrofuran, benzonitriles, dimethylsulfoxide, tetramethylene sulfone, carbon disulfide, and benzene rings substituted with at least one halide such as chlorobenzene, dichlorobenzene, trichlorobenzene, fluorobenzene, difluorobenzene, trifluorobenzene, bromobenzene, dibromobenzene, tribromobenzene, or mixtures thereof.

The products of the present process include halo-bisaryl-1,3,5-triazine compounds or trisaryl-1,3,5-triazine compounds wherein the aromatic compounds include a $C_5$-$C_{24}$ unsaturated ring, such as cyclopentadiene, phenyl, biphenyl, indene, naphthalene, tetralin, anthracene, phenanthrene, benzonaphthene, fluorene, which may be substituted in one or more positions with a halide, an hydroxyl, an ether, a polyether, a thiol, a thioether, an amine, such as —NHR, —$NR_2$, —NRR', a carboxylic acid, an ester, an amide or a $C_1$-$C_{12}$ group which may be saturated or unsaturated and cyclic or non-cyclic, and which optionally may be substituted with any of the above preceding groups. A general structure of useful compounds is shown above in Formulas I and III.

Preferred products include chloro-bisaryl-1,3,5-triazine compounds or trisaryl-1,3,5-triazine compounds wherein the aromatic substituents include phenyl, an ortho, meta, and/or para substituted phenyl ring, a naphthalene ring substituted at one or more positions, substituted or unsubstituted biphenyl, or tetralin ring substituted at one or more positions, wherein the substitution group is a lower alkyl such as methyl, ethyl, propyl, butyl, iso-butyl, t-butyl, pentyl, hexyl, septyl, octyl, nonyl, hydroxy, an ether group such as methoxy, ethoxy, propyloxy, octyloxy, nonyloxy, or a halogen, such as fluoride, chloride, bromide, or iodide.

Other suitable products include chloro-bisaryl-1,3,5-triazine compounds, trisaryl-1,3,5-triazine compounds, or 2-(2-oxyaryl)-4,6-bisaryl-1,3,5-triazine compounds wherein the aromatic substituted compounds include o-xylene, m-xylene, p-xylene, o-cresol, m-cresol, p-cresol, mesitylene, trimethylbenzene, cumene, anisole, ethoxybenzene, benzene, toloune, ethylbenzene, biphenyl, tert-butylbenzene, propoxybenzene, butoxybenzene, o-methoxyphenol, m-methoxyphenol, p-methoxyphenol, o-ethoxyphenol, m-ethoxyphenol, p-ethoxyphenol, o-nonoxyphenol, m-nonoxyphenol, tetralin, 2-chloro-4,6-bis(2,4-dimethylphenyl)-1,3,5-triazine; 2-(2,4-dihydroxyphenyl)-4,6-bis(2,4-dimethylphenyl)-1,3,5-triazine; 2-(4-alkoxy-2-hydroxyphenyl)-4,6-bis(2,4-dimethylphenyl)-1,3,5-triazine; 2-chloro-4,6-bisphenyl-1,3,5-triazine; 2-(2,4-dihydroxyphenyl)-4,6-bisphenyl-1,3,5-triazine; 2-(4-alkoxy-2-hydroxyphenyl)-4,6-bisphenyl-1,3,5-triazine; 2-(2-hydroxy-4-octyloxyphenyl)-4,6-bis(2,4-dimethylphenyl)-1,3,5-triazine; 2-(2-hydroxy-4-hexyloxyphenyl)-4,6-bis(2,4-dimethylphenyl)-1,3,5-triazine; and 2-(2-hydroxy-4-isooctyloxyphenyl)-4,6-bis(2,4-dimethylphenyl)-1,3,5-triazine.

The term "step-wise" means a reaction sequence wherein a series of reactions are conducted, the first reaction producing a compound of Formula IV and being carried out to about 50% to about 100% completion prior to addition of a compound of Formula IV to produce a compound of Formula I. Preferably the reaction is carried out to about 70% to about 100% completion prior to addition of compound of Formula IV, and more preferably to about 75% to about 100% completion.

The term "continuous" means a reaction sequence not defined as "step-wise."

The relative amounts of the reactants are as follows. The amount of a cyanuric halide should be in sufficient amounts to react with aromatic compounds of Formula II to produce either 2-halo-4,6-bisaryl-1,3,5-triazine or 2,4,6-trisaryl-1,3,5-triazine. The amount of aromatic compound of Formula II is important to ensure that a sufficient amount of monohalo-bisaryl-triazine is synthesized without excessive amounts of undesired side products such as 2,4-dihalo-6-aryl-1,3,5-triazine or trisaryl triazine. Moreover, excess amounts of aromatic compounds can lead to undesired product distributions enriched in mono- and tris-aryl triazines, thus, making product separation and purification difficult and resource consuming.

The amount of aromatic compounds should be in sufficient amounts to synthesize 2-halo-4,6-bisaryl-1,3,5-triazine, 2,4,6-trisaryl-1,3,5-triazine, or convert 2-halo-4,6-bisaryl-1,3,5-triazine into 2,4,6-trisaryl-1,3,5-triazine. Preferably, there should be between about 1 to about 5 mol equivalents of aromatic compound of formula II to cyanuric halide. More preferably, the amount of aromatic compound of Formula IV should be between about 0.5 to about 2.5 mol equivalents of aromatic compound of Formula IV to cyanuric halide. In some cases aromatic compounds of Formula II can be used both as a reactant and a solvent.

The amount of Lewis acid used in the reaction facilitator should be in sufficient amounts to transform 2,4,6-trihalo-1,3,5-triazine to the preferred 2-halo-4,6-bisaryl-1,3,5-triazine or 2,4,6-trisaryl-1,3,5-triazine. The amount of Lewis acid should be between about 0.5 to about 500 mol equivalents. Preferably, the amount of Lewis acid should be between about 1 to about 10 mol equivalents to cyanuric halide.

The amount of reaction promoter used in the reaction facilitator should be in sufficient amounts to transform 2,4,6-trihalo-1,3,5-triazine, to the preferred 2-halo-4,6-bisaryl-1,3,5-triazine or convert 2-halo-4,6-bisaryl-1,3,5-triazine to the compound of Formula I. Preferably, the amount of reaction promoter should be between about 0.01 to about 5 mol equivalents to cyanuric halide.

The Lewis acid and reaction promoter preferably combine to form a reaction facilitator complex that can be prepared in situ or pre-formed prior to addition to the reagents. The Lewis acid and/or reaction promoter or reaction facilitator can be combined with either a compound of Formula II or compound of Formula IV or both in any manner. In situ reaction facilitator preparation comprises addition of at least one Lewis acid and at least one reaction promoter to a mixture of cyanuric halide, at least one aromatic compound of Formula II, and optionally solvent without regard to addition order. To prepare the reaction facilitator prior to addition to the reagents, i.e., the pre-formed method, Lewis acid and reaction promoter are combined and allowed to mix prior to addition, optionally in an inert solvent. Thereafter, the reaction facilitator is added to the reagents or vice versa, as desired and in any addition order. As used herein, one or more Lewis acids may be used, the first step and second step Lewis acid may be the same or different. Additionally, one or more reaction promoters may be used, the first step and second step reaction promoter may be the same or different. In the "continuous-"process, the use of additional Lewis acid and reaction promoter is optional.

If the reaction facilitator is prepared using the pre-formed method, preferred mixing time of the Lewis acid and reaction promoter; prior to addition to the reagents, is between about 1 minute to about 10 hours, more preferred is between about 10 minutes to about 5 hours. The preferred mixing temperature of the Lewis acid and reaction promoter combination, prior to addition to the reagents, is between about −50° C. to about 100° C., more preferred is between about −10° C. to about 50° C.

The reaction should run for sufficient time, at a sufficient temperature and pressure to synthesize the desired triazine compound. The preferred reaction time fort the synthesis of compounds of Formula III, i.e., the first step, is between about 5 minutes and about 48 hours, more preferred between about 15 minutes and about 24 hours. The preferred reaction time for the synthesis of compounds of Formula I, i.e., the second step, is between about 10 minutes and about 24 hours, more preferably between about 30 minutes and about 12 hours. The use of the reaction facilitator reduces the reaction time while improving the selectivity for mono-halo-bis-aryl products in the first step. The preferred reaction temperature for the first step is between about −50° C. and about 150° C., more preferred between about −30° C. and about 50° C. One advantage of using the reaction facilitator is the elimination of the need to heat the reaction mixture to increase the rate of reaction. Additionally, due to the use of the reaction facilitator, the reaction temperature can be maintained at about ambient or lower temperatures, thus increasing product selectivity. The reaction pressure is not critical and can be about 1 atm or higher if desired. An inert gas such as nitrogen or argon is preferred. The preferred reaction temperature for the second step is between about 0° C. and about 120° C., more preferred between about 20° C. and about 100° C.

The step-wise process comprises mixing cyanuric halide and the reaction facilitator with one or more of the desired aromatic compounds, preferably until the reaction is about 70% to about 100% completed. Thereafter, the product of Formula III is isolated. The second aromatic compound of Formula IV is added to the isolated product of Formula III along with Lewis acid and optionally reaction promoter or reaction facilitator to synthesize the trisaryl-triazine. The step-wise sequence allows for the isolation, purification, and storage of Formula III product prior to subsequent reaction with compounds of Formula IV.

The continuous reaction comprises allowing a cyanuric halide to react with one or more aromatic compounds of Formula II in the presence of the reaction facilitator preferably until the reaction is about 70% to about 100% complete. Thereafter, without isolating the product of Formula III, the second aromatic compound of Formula IV is allowed to react with the product of Formula III in the presence of optionally at least one second Lewis acid and optionally at least one second reaction promoters, or reaction facilitator preferably until the reaction is about 70% to about 100% complete. The continuous reaction eliminates the need to isolate the intermediate product of Formula III or use of additional reagents such as solvents, and optionally Lewis acids, reaction promoters, or reaction facilitators. Moreover, the one-step process simplifies the synthetic reaction pathway such that no unnecessary handling or processing of the reaction mixture is required until the reaction is completed.

To synthesize compounds of Formula III using the pre-formed reaction facilitator method, the preferred addition time of the reaction facilitator to a reagent mixture is between about 5 minutes to about 5 hours, more preferred is between about 15 minutes to about 3 hours. The addition temperature of the reaction facilitator to a reagent mixture is between about −50° C. to about 150° C., preferred addition temperature is between about −30° C. to about 50° C., and more preferred addition temperature between about −20° C. to about 30° C.

To synthesize compounds of Formula I using the pre-formed reaction facilitator, the preferred addition temperature of the reaction facilitator to a reagent mixture is between about 0° C. to about 100° C., preferred addition temperature is between about 20° C. to about 80° C.

To synthesize compounds of Formula I, the preferred addition time of the compound of Formula IV to the reaction mixture is between about 5 minutes to about 10 hours, more preferred addition time is between about 10 minutes to about 5 hours, and most preferred addition time is between about 15 minutes to about 2 hours. The addition temperature of the compound of Formula IV to the reaction mixture is between about 0° C. to about 150° C., preferred addition temperature is between about 20° C. to about 100° C.

The reaction facilitator should be present in amounts sufficient to react with the number of halogens being substituted on the triazine compound. A range of between about 1 to about 10 mol equivalents of Lewis acid and a range of between about 0.01 to about 5 mol equivalents of reaction promoter can be used. The preferred Lewis acid is aluminum halide, most preferably aluminum chloride. A preferred amount of Lewis acid is between about 2 to about 4 mol equivalents to halo-triazine. A preferred amount of reaction promoter is between about 0.05 to about 2 mol equivalents to triazine or triazine derived compounds.

The invention provides several advantages over prior art process such as higher yields, greater selectivity of reaction products, higher reaction rates, and/or applicability of reaction conditions to various aromatic compounds. The present invention consistently provided yields in the range of about 70 to about 98%, based on cyanuric halide conversion, as determined by HPLC analysis. Additionally, the ratio of desired 2-halo-4,6-bisaryl-1,3,5-triazine to trisaryl-1,3,5-triazine consistently averaged about 70:30 or more. The reaction facilitator significantly increased reaction rates in comparison to state of the art with Lewis acids alone. Moreover, the reaction conditions provided high yield and selectivity for a variety of aromatic compounds regardless oft the aromatic substituents.

The triazine compounds synthesized using the present process can be applied to a variety of applications such as those described in U.S. Pat. No. 5,543,518 to Stevenson et al. Col. 10-19, the content of which, as noted above, is expressly incorporated by reference herein.

The 2-chloro-4,6-bisaryl-1,3,5-triazines are not only important intermediates for the preparation of trisaryl triazine UV absorbers, but they are also valuable intermediates for a variety of other commercially important products, such as vat dyestuffs (GB 884,802), photographic material (JP 09152701 A2), optical materials (JP 06065217 A2), and polymers (U.S. Pat. No. 706,424; DE 2053414, DE 1246238). These compounds are also of interest for medicinal applications (e.g., see: R. L. N. Harris, *Aust. J. Chem.*, 1981, 34, 623-634; G. S. Trivedi, A. J. Cowper, R. R. Astik, and K. A. Thaker, *J. Inst. Chem.*, 1981, 53(3), 135-138 and 141-144).

EXAMPLES

Certain embodiments and features of the invention are illustrated, and not limited, by the following working examples.

The reaction progress can be monitored by HPLC or TLC. Further product characterization may be done by LCMS, MS, NMR, UV, direct comparison with authentic examples, or analytical techniques which are well known in the art. A typical HPLC analysis of the samples is carried out as follows. The reaction mixture may, in some cases be a two-phase system, with a lower, viscous liquid layer which may contain most of the reaction products (as $AlCl_3$ complexes), and a supernatant, which may contain very little material. This supernatant can be often enriched in unreacted cyanuric chloride. In case of a two-phase system, it is important that both phases are sampled together, in a representative fashion. For example, the mixture can be stirred rapidly and a sample taken from the middle of the mixture using a polyethylene pipette with the tip cut off. When pipetting the sample into a vial for work-up, it is important that the contents of the pipette be completely discharged. Since the two phases will separate into upper and lower layers, partial discharge may result in a sample enriched in the lower layer.

The reaction sample is discharged into a 4-dram vial containing either chilled 5% HCl, or a mixture of 5% HCl and ice. The precipitate can be extracted with ethyl acetate and the water layer can be pipetted off. The ethyl acetate layer is then washed with water. Finally, an approximately 10% solution of the ethyl acetate layer in acetonitrile is prepared for HPLC analysis.

Certain embodiments and features of the invention are illustrated, and not limited, by the following working examples.

Example 1

Synthesis of 2-chloro-4,6-bis(2,4-dimethylphenyl)-1,3,5-triazine without a Reaction Promoter Cyanuric chloride (1.84 g) was allowed to react with 1.9 eq of m-xylene and 2.5 eq (3.35 g) of $AlCl_3$ in 25 mL of chlorobenzene at 5° C. for 0.5 h and then at room temperature for 3 h. Analysis by HPLC, after 2.5 h, showed that less than 8% of cyanuric chloride had reacted to form only 2,4-dichloro-6-(2,4-dimethylphenyl)-1,3,5-triazine, no 2-chloro-4,6-bis(2,4-dimethylphenyl)-1,3,5-triazine or 2,4,6-tris(2,4-dimethylphenyl)-1,3,5-triazine were present. The reaction was allowed to continue at room temperature. After 24 hours, HPLC analysis showed about 51% cyanuric chloride conversion and formation of 2,4 dichloro-6-(2,4-dimethylphenyl)-1,3,5-triazine and 2-chloro-4,6-bis(2,4-dimethylphenyl)-1,3,5-triazine in the ratio of 95:5, respectively No 2,4,6-tris(2,4-dimethylphenyl)-1,3,5-triazine was detected.

Example 2

Synthesis of 2-chloro-4,6-bis(2,4-dimethylphenyl)-1,3,5-triazine without a Reaction Promoter Cyanuric chloride (1.84 g) was allowed to react with 2.05 eq of m-xylene and 2.5 eq (3.35 g) of $AlCl_3$ in chlorobenzene at 5° C. for 2 h and then at 15° C. for 5 h. Analysis by HPLC showed about 5% conversion of cyanuric chloride to 2,4-bischloro-6-(2,4-dimethylphenyl)-1,3,5-triazine and no 2-chloro-4,6-bis(2,4-dimethylphenyl)-1,3,5-triazine or 2,4,6-tris(2,4-dimethylphenyl)-1,3,5-triazine. The reaction was allowed to continue at room temperature. After 22 hours, HPLC analysis showed about 55% cyanuric chloride conversion and formation of 2,4-dichloro-6-(2,4-dimethylphenyl)-1,3,5-triazine and 2-chloro-4,6-bis(2,4-dimethylphenyl)-1,3,5-triazine in the ratio of 96:4, respectively. The reaction was allowed to continue. After 72 hours at room temperature, a final HPLC analysis showed 99% cyanuric chloride conversion, formation of 2-chloro-4,6-bis(2,4-dimethylphenyl)-1,3,5-triazine and 2,4,6-tris(2,4-dimethylphenyl)-1,3,5-triazine in the ratio of 78:22, and no 2,4-bischloro-6-(2,4-dimethylphenyl)-1,3,5-triazine was detected.

Example 3

Synthesis of 2-chloro-4,6-bis(2,4-dimethylphenyl)-1,3,5-triazine using 0.1 eq resorcinol and 2.5 eq $AlCl_3$ Cyanuric chloride was allowed to react with 2.05 eq of m-xylene in chlorobenzene, in the presence of 2.5 eq of $AlCl_3$ and 0.1 eq of resorcinol. The reaction was carried out at about 5° C. for 2 h and then at room temperature for 5 h. Analysis by HPLC showed about 10% conversion of cyanuric chloride to 2,4-dichloro-6-(2,4-dimethylphenyl)-1,3,5-triazine. After about 40 h at room temperature, HPLC analysis showed 99% cyanuric chloride conversion to 2-chloro-4,6-bis(2,4-dimethylphenyl)-1,3,5-triazine and 2,4,6-tris(2,4-dimethylphenyl)-1,3,5-triazine present in a 78:22 ratio respectively, no 2,4-dichloro-6-(2,4-dimethylphenyl)-1,3,5-triazine was detected.

Example 4

Synthesis of 2-chloro-4,6-bis(2,4-dimethylphenyl)-1,3,5-triazine using 0.2 eq resorcinol and 2.5 eq $AlCl_3$ and conversion to 2-(2,4-dihydroxyphenyl)-4,6-bis(2,4-dimethylphenyl)-1,3,5-triazine Cyanuric chloride (1.84 g) was allowed to react with 1.9 eq of m-xylene, in the presence of 2.5 eq of $AlCl_3$ (3.35 g) and 0.2 eq of resorcinol, in 25 mL chlorobenzene at bout 5° C. for 0.5 h and then at room temperature for 3 h. Analysis by HPLC showed about 14% conversion of cyanuric chloride to 2,4-dichloro-6-(2,4-dimethylphenyl)-1,3,5-triazine. After about 13 h at room temperature, HPLC analysis showed 99% cyanuric chloride conversion to 2-chloro-4,6-bis(2,4-dimethylphenyl)-1,3,5-triazine and 2,4,6-tris(2,4-dimethylphenyl)-1,3,5-triazine, in a ratio of 82:18, respectively. No 2,4-dichloro-6-(2,4-dimethylphenyl)-1,3,5-triazine or resorcinol-containing products were detected.

To the reaction mixture was added an additional 0.9 eq resorcinol and the reaction mixture was heated at 80° C. for 1 h. HPLC analysis indicated the formation of 2-(2,4-dihydroxyphenyl)-4,6-bis(2,4-dimethyl)-1,3,5-triazine and 2,4,6-tris(2,4-dimethylphenyl)-1,3,5-triazine in a 79:21 ratio, with about 1% unreacted 2-chloro-4,6-bis(2,4-dimethylphenyl)-1,3,5-triazine. The process to make 2-(2,4-dihydroxyphenyl)-4,6-bis(2,4-dimethylphenyl)-1,3,5-triazine was complete within 15 hours.

The heating was discontinued and the reaction mixture allowed to cool to room temperature. 2% ice-cold aqueous HCl was added with stirring to break the aluminum complexes. A yellow precipitate was formed. The reaction mixture was filtered, washed with water, and dried to give 3.65 g of crude 2-(2,4-dihydroxyphenyl)-4,6-bis(2,4-dimethylphenyl)-1,3,5-triazine.

Example 5

Synthesis of 2-(2,4-dihydroxyphenyl)-4,6-bis(2,4-dimethylphenyl)-1,3,5-triazine using 1 eq resorcinol and 2.5 eq $AlCl_3$ Cyanuric chloride (1.84 g) was allowed to react with 2.05 eq of m-xylene, in the presence of 2.5 eq of $AlCl_3$ (3.35 g) and 1 eq of resorcinol, in 25 mL chlorobenzene at about 5° C. for 2 h and then at 15° C. for 4 h. Analysis by HPLC showed 70% conversion of cyanuric chloride, mainly to 2-chloro-4,6-bis(2,4-dimethylphenyl)-1,3,5-triazine and 2,4,6-tris(2,4-dimethylphenyl)-1,3,5-triazine in a 59:41 ratio. Two minor components were also present, 2,4-dichloro-6-(2,4-dimethylphenyl)-1,3,5-triazine (5%) and 2-(2,4-dihydroxyphenyl)-4,6-bis(2,4-dimethylphenyl)-1,3,5-triazine (3%). The reaction mixture was allowed to warm to room temperature, and after about 16 h at room temperature, HPLC analysis showed 92% cyanuric chloride conversion, mainly to 2,4,6-tris(2,4-dimethylphenyl)-1,3,5-triazine (66%), 2-(2,4-dihydroxyphenyl)-4,6-bis(2,4-dimethylphenyl)-1,3,5-triazine (25%), 2-chloro-4,6-bis(2,4-dimethylphenyl)-1,3,5-triazine (4.5%), and 2,4-dichloro-6-(2,4-dimethylphenyl)-1,3,5-triazine and 2-chloro-4-(2,4-dihydroxyphenyl)-6-(2,4-dimethylphenyl)-1,3,5-triazine (3%).

Example 6

Synthesis of 2-(2,4-dihydroxyphenyl)-4,6-bis(2,4-dimethylphenyl)-1,3,5-triazine using 0.5 eq resorcinol and 2.5 eq $AlCl_3$ Cyanuric chloride was allowed to react with 2 eq of m-xylene, in the presence of 2.5 eq of $AlCl_3$ and 0.5 eq of resorcinol, in chlorobenzene at room temperature for about 22 h. Analysis of the reaction mixture by HPLC showed about 94% cyanuric chloride conversion, mainly to 2,4,6-tris(2,4-dimethylphenyl)-1,3,5-triazine, 2-chloro-4,6-bis(2,4-dimethylphenyl)-1,3,5-triazine and 2-(2,4-dihydroxyphenyl)-4,6-bis(2,4-dimethylphenyl)-1,3,5-triazine in a ratio of 69:27:4.

Example 7

Synthesis of chloro-4,6-bis(2,4-dimethylphenyl)-1,3,5-triazine using 3 eq $AlCl_3$ A. Absence of a Reaction Promoter Cyanuric chloride was allowed to react with 2.05 eq of m-xylene, in the presence of 3 eq of $AlCl_3$, in chlorobenzene at 5° C. for 0.5 h and then at room temperature for 3 h. An HPLC analysis showed about 3% cyanuric chloride conversion to 2,4-dichloro-6-(2,4-dimethylphenyl)-1,3,5-triazine; no 2-chloro-4,6-bis(2,4-dimethylphenyl)-1,3,5-triazine or 2,4,6-tris(2,4-dimethylphenyl)-1,3,5-triazine was detected. After 24 h at room temperature, HPLC analysis showed about 33% conversion to cyanuric chloride to 2,4-dichloro-6-(2,4-dimethylphenyl)-1,3,5-triazine and 2-chloro-4,6-bis(274-dimethylphenyl)-1,3,5-triazine, formed in a 96:4 ratio respectively.

B. Effect of 0.2 eq of Resorcinol

Thereafter, 0.2 eq of resorcinol was added to the above reaction mixture, and the reaction mixture was further stirred at room temperature for 16 h. HPLC analysis showed 97% cyanuric chloride conversion to 2-chloro-4,6-bis(2,4-dimethylphenyl)-1,3,5-triazine and 2,4,6-tris(2,4-dimethylphenyl)-1,3,5-triazine, formed in an 80:20 ratio respectively; no 2,4-dichloro-6-(2,4-dimethylphenyl)-1,3,5-triazine was detected.

Example 8

Synthesis of 2-(2,4-dihydroxyphenyl)-4,6-bis(2,4-dimethylphenyl)-1,3,5-triazine using 0.2 eq resorcinol and 3 eq $AlCl_3$ Cyanuric chloride was allowed to react with 1.9 eq of m-xylene, in the presence of 3 eq of $AlCl_3$ and 0.2 eq of resorcinol, in chlorobenzene at 5° C. for 0.5 h and then at room temperature for 3 h. Am HPLC analysis after 3 h at room temperature showed about 20% cyanuric chloride conversion to 2-chloro-4,6-bis(2,4-dimethylphenyl)-1,3,5-triazine. The reaction mixture was stirred overnight at room temperature. After 18 h, an HPLC analysis showed 97% cyanuric chloride conversion to 2-chloro-4,6-bis(2,4-dimethylphenyl)-1,3,5-triazine and 2,4,6-tris(2,4-dimethylphenyl)-1,3,5-triazine, formed in an 81:19 ratio respectively; no 2,4-dichloro-6-(2,4-dimethylphenyl)-1,3,5-triazine was detected.

To the reaction mixture was then added 0.9 eq of resorcinol, and the mixture was heated in an oil bath to 60° C. (oil bath temperature). After 5 h, analysis by HPLC showed the formation of 2-(2,4-dihydroxyphenyl)-4,6-bis(2,4-dimethylphenyl)-1,3,5-triazine (73%) and 2,4,6-tris(2,4-dimethylphenyl)-1,3,5-triazine (21%), with 3% of unreacted 2-chloro-4,6-bis(2,4-dimethylphenyl)-1,3,5-triazine.

Example 9

Synthesis of 2-(2,4-dihydroxyphenyl)-4,6-bis(2,4-dimethylphenyl)-1,3,5-triazine using 0.2 eq resorcinol and 2.75 eq $AlCl_3$ Cyanuric chloride was allowed to react with 2.05 eq of m-xylene in the presence of 2.75 eq of $AlCl_3$, and 0.2 eq of resorcinol in chlorobenzene at 5° C. for 0.5 h and then allowed to warm to room temperature. After a total of 18 h at room temperature, analysis by HPLC showed 98% cyanuric chloride conversion to 2-chloro-4,6-bis(2,4-dimethylphenyl)-1,3,5-triazine and 2,4,6-tris(2,4-dimethylphenyl)-1,3,5-triazine in an 81:19 ratio respectively; no 2,4-dichloro-6-(2,4-dimethylphenyl)-1,3,5-triazine was detected. The reaction mixture was then allowed to react with 0.9 eq of resorcinol at 60° C. for 5 h. HPLC analysis showed the formation of 2-(2,4-dihydroxyphenyl)-4,6-bis(2,4-dimethylphenyl)-1,3,5-triazine and 2,4,6-tris(2,4-dimethylphenyl)-1,3,5-triazine in a ratio of 77:21 with 1% unreacted 2-chloro-4,6-bis(2,4-dimethylphenyl)-1,3,5-triazine.

Example 10

Synthesis of 2-(2,4-dihydroxyphenyl)-4,6-bis(2,4-dimethylphenyl)-1,3,5-triazine using 0.2 eq resorcinol and 1.8 eq $AlCl_3$ Cyanuric chloride was allowed to react with 2.05 eq of m-xylene, in the presence of 1.8 eq of $AlCl_3$, and 0.2 eq of resorcinol in chlorobenzene at 5° C. for 0.5 h and then allowed to warm to room temperature. After 18 h at room temperature, HPLC analysis showed 84% cyanuric chloride conversion to 2-chloro-4,6-bis(2,4-dimethylphenyl)-1,3,5-triazine and 2,4,6-tris(2,4-dimethylphenyl)-1,3,5-triazine, formed in a 46:54 ratio. 2,4,6-tris(2,4-dimethylphenyl)-1,3,5-triazine was the major product, and about 3% 2,4-dichloro-6-(2,4-dimethylphenyl)-1,3,5-triazine was also present.

The reaction was allowed to continue at room temperature. After 4 days, HPLC analysis showed 93% cyanuric chloride conversion, with the following product distribution: 75% 2,4,6-tris(2,4-dimethylphenyl)-1,3,5-triazine; 17% 2-(2,4-dihydroxyphenyl)-4,6-bis(2,4-dimethylphenyl)-1,3,5-triazine; 4% 2-chloro-4,6-bis(2,4-dimethylphenyl)-1,3,5-triazine; and other resorcinol-containing components as minor products.

Example 11

Synthesis of 2-(2,4-dihydroxyphenyl)-4,6-bis(2,4-dimethylphenyl)-1,3,5-triazine using 0.144 eq resorcinol and 1.8 eq $AlCl_3$ Cyanuric Chloride was allowed to react with 2.05 eq of m-xylene, in the presence of 1.8 eq of $AlCl_3$ and 0.144 eq of resorcinol, in chlorobenzene at 5° C. for 0.5 h and then at room temperature for 3 h. The ratio of $AlCl_3$ to resorcinol was thus 12.5:1. An HPLC analysis after 65 hours at room temperature showed 91% cyanuric chloride conversion, with the following product distribution: 79% 2,4,6-tris(2,4-dimethylphenyl)-1,3,5-triazine; 10% 2-(2,4-dihydroxyphenyl)-4,6-bis(2,4-dimethylphenyl)-1,3,5-triazine; 8% 2-chloro-4,6-bis(2,4-dimethylphenyl)-1,3,5-triazine; and other resorcinol-containing compounds as minor products Example 12

Synthesis of 2-(2,4-dihydroxyphenyl)-4,6-bis(2,4-dimethylphenyl)-1,3,5-triazine using 0.15 eq resorcinol and 2.5 eq $AlCl_3$ in a tetrachloroethane solvent Cyanuric chloride was allowed to react with 1.9 eq of m-xylene, in the presence of 0.15 eq of resorcinol and 2.5 eq of $AlCl_3$, in 1,1,2,2-tetrachloroethane at room temperature for about 26 h. HPLC analysis showed about 95% cyanuric chloride conversion to 2-chloro-4,6-bis(2,4-dimethylphenyl)-1,3,5-triazine and 2,4,6-tris(2,4-dimethylphenyl)-1,3,5-triazine, formed in an 87:13 ratio. The reaction mixture was allowed to react with an additional 0.9 eq of resorcinol for 4 h at 90° C. HPLC analysis showed 98.3% 2-chloro-4,6-bis(2,4-dimethylphenyl)-1,3,5-triazine conversion, and the ratio of 2-(2,4-dihydroxyphenyl)-4,6-bis(2,4-dimethylphenyl)-1,3,5-triazine to 2,4,6-tris(2,4-dimethylphenyl)-1,3,5-triazine was 84:16.

Example 13

Synthesis of 2-(2,4-dihydroxyphenyl)-4,6-bis(2,4-dimethylphenyl)-1,3,5-triazine using 0.2 eq resorcinol and 3 eq $AlCl_3$ in a tetrachloroethane solvent Cyanuric chloride was allowed to react with 2.05 eq of m-xylene, in the presence of 3 eq of $AlCl_3$ and 0.2 of resorcinol, in chlorobenzene at 5° C. for 0.5 h and then at room temperature for 3 h. The first step (conversion to 2-chloro-4,6-bis(2,4-dimethylphenyl)-1,3,5-triazine) was completed in less than 16 h, with more than 98% cyanuric chloride conversion as determined by HPLC analysis. 2-chloro-4,6-bis(2,4-dimethylphenyl)-1,3,5-triazine and 2,4,6-tris(2,4-dimethylphenyl)-1,3,5-triazine were formed in an 86:14 ratio; no other products were detected. The reaction mixture was allowed to react with additional resorcinol at 110° C. for 1.5 h. HPLC analysis showed a product mixture of 82% 2-(2,4-dihydroxyphenyl)-4,6-bis(2,4-dimethylphenyl)-1,3,5-triazine, 14% 2,4,6-tris(2,4-dimethylphenyl)-1,3,5-triazine, and 2% 2,4,6-tris(2,4-dihydroxyphenyl)-1,3,5-triazine, with only 1.5% unreacted 2-chloro-4,6-bis(2,4-dimethylphenyl)-1,3,5-triazine.

Example 14

Synthesis of 2-(2,4-dihydroxyphenyl)-4,6-bis(2,4-dimethylphenyl)-1,3,5-triazine using methyl alcohol with 3 eq $AlCl_3$ A two-neck round bottom flask was equipped with a reflux condenser; an argon inlet, a magnetic stirring bar and a glass stopper Cyanuric chloride (3.7 g) and 50 mL of chlorobenzene were added. Next, 3 eq of $AlCl_3$ (8 g) at ice-bath temperature was added, followed by 0.4 mL of methyl alcohol. After 5 min, 1.9 eq of m-xylene was added. The cooling was removed, and the reaction mixture was stirred at room temperature. The reaction was complete within 20 h at room temperature, as indicated by HPLC which showed the absence of m-xylene and 97% conversion of cyanuric chloride to 2-chloro-4,6-bis(2,4-dimethylphenyl)-1,3,5-triazine and 2,4,6-tris(2,4-dimethylphenyl)-1,3,5-triazine in an 83:17 ratio.

To the reaction mixture was added 1.1 eq of resorcinol, and the reaction mixture was heated at 85° C. for 4.5 h. HPLC analysis showed the formation of 78% 2-(2,4-dihydroxyphenyl)-4,6-bis(2,4-dimethylphenyl)-1,3,5-triazine, 19% 2,4,6-tris(2,4-dimethylphenyl)-1,3,5-triazine, 1.6% unreacted 2-chloro-4,6-bis(2,4-dimethylphenyl)-1,3,5-triazine, and 1.4% 2,4,6-tris(2,4-dihydroxylphenyl)-1,3,5-triazine. The reaction was allowed to cool to room temperature, and 2% ice-cold aqueous HCl was added. A yellow precipitate was formed, separated by filtration, washed with water, and dried to yield 7.7 g of crude 2-(2,4-dihydroxyphenyl)-4,6-bis(2,4-dimethylphenyl)-1,3,5-triazine.

Example 15

Synthesis of 2-chloro-4,6-bis(2,4-dimethylphenyl)-1,3,5-triazine using 0.2 eq resorcinol and 2.5 AlCl$_3$ at 45° C.

Cyanuric chloride was allowed to react with 1.9 eq m-xylene, in the presence of 2.5 eq AlCl$_3$ and 0.2 eq resorcinol, in chlorobenzene at 45° C. HPLC analysis of the reaction after 4 h showed 95% conversion of cyanuric chloride to 2-chloro-4,6-bis(2,4-dimethylphenyl)-1,3,5-triazine and 2,4,6-tris(2,4-dimethylphenyl)-1,3,5-triazine, which were formed in a 67:33 ratio respectively.

Example 16

Synthesis of 2-(2,4-dihydroxyphenyl)-4,6-bis(2,4-dimethylphenyl)-1,3,5-triazine using 0.2 eq resorcinol and 2.5 eq AlCl$_3$ in a dichlorobenzene solvent Cyanuric chloride was allowed to react with 2 eq m-xylene, in the presence of 2.5 eq AlCl$_3$ and 0.2 eq of resorcinol, in ortho-dichlorobenzene at 24° C. After about 21 h, an exotherm was observed. A sample was immediately taken. HPLC analysis of the sample showed 94% conversion of cyanuric chloride to 2-chloro-4,6-bis(2,4-dimethylphenyl)-1,3,5-triazine and 2,4,6-tris(2,4-dimethylphenyl)-1,3,5-triazine, in an 81:19 ratio. After the exotherm had subsided, the cyanuric chloride conversion had increased to 97.5%, and the 2-chloro-4,6-bis(2,4-dimethylphenyl)-1,3,5-triazine to 2,4,6-tris(2,4-dimethylphenyl)-1,3,5-triazine ratio was 79:21.

To this mixture was added 0.9 eq additional resorcinol, and the mixture was heated to 80° C. for 1 h. HPLC analysis of the reaction showed 2-(2,4-dihydroxyphenyl)-4,6-bis(2,4-dimethylphenyl)-1,3,5-triazine, with a 2-(2,4-dihydroxyphenyl)-4,6-bis(2,4-dimethylphenyl)-1,3,5-triazine to 2,4,6-tris(xylyl)-1,3,5-triazine ratio of 77:23, and about 2% unreacted bisaryl-chloro-triazine.

Example 17

Synthesis of 2-chloro-4,6-bis(2,4-dimethylphenyl)-1,3,5-triazine using 0.2 eq resorcinol and 2.5 eq AlCl$_3$ in a dichlorobenzene solvent A. No Cooling during Exotherm Cyanuric chloride was allowed to react with 2 eq m-xylene, in the presence of 2.5 eq AlCl$_3$ and 0.2 eq of resorcinol, in ortho-dichlorobenzene at 40° C. A 4° C. exotherm was observed after 4-5 h. HPLC analysis of the reaction at this point showed 96% conversion of cyanuric chloride to 2-chloro-4,6-bis(2,4-dimethylphenyl)-1,3,5-triazine and 2,4,6-tris(2,4-dimethylphenyl)-1,3,5-triazine, which were formed in a 78:22 ratio.

B. With Cooling to 10° C. after 4 h

The reaction of part (A) was repeated. The exotherm began after 4 h. A sample was immediately taken, and the reaction was cooled to 10° C. HPLC analysis of the sample showed 96% conversion of cyanuric chloride to 2-chloro-4,6-bis(2,4-dimethylphenyl)-1,3,5-triazine and 2,4,6-tris(2,4-dimethylphenyl)-1,3,5-triazine, which were formed in a 78:22 ratio. There was also some unreacted 2,4-dichloro-6-(2,4-dimethylphenyl)-1,3,5-triazine at this point. After 1 h at 10° C., the cyanuric chloride conversion was 97%, no 2,4-dichloro-6-(2,4-dimethylphenyl)-1,3,5-triazine was detected, and the ratio of 2,4-dichloro-6-(2,4-dimethylphenyl)-1,3,5-triazine to 2,4,6-tris(2,4-dimethylphenyl)-1,3,5-triazine was 83:17.

Example 18

Synthesis of 2-(2,4-dihydroxyphenyl)-4,6-bis(2,4-dimethylphenyl)-1,3,5-triazine using 0.2 eq resorcinol and 3 eq AlCl$_3$ with 6.5% concentrated HCl To a stirring mixture of 1 eq of cyanuric chloride, 3 eq of AlCl$_3$ and 0.2 eq of resorcinol in chlorobenzene, was added 6.5% (based on the weight of cyanuric chloride) of concentrated HCl at ice-bath temperature. An immediate reaction with AlCl$_3$ was observed, leading to its almost complete solvation of AlCl$_3$. 1.9 eq of m-xylene was then added. Within 5 min the color changed from light yellow to dark yellow to orange and finally dark red. The cooling bath was removed and the reaction mixture was analyzed at this stage by HPLC. The HPLC analysis showed 99% cyanuric chloride conversion to 2-chloro-4,6-bis(2,4-dimethylphenyl)-1,3,5-triazine and 2,4,6-tris(2,4-dimethylphenyl)-1,3,5-triazine, which were formed in a 92:8 ratio. Thereafter, the reaction mixture was allowed to react with 1.1 eq of resorcinol and subsequently, heated between 85°-90° C. for 1 h. HPLC analysis of the reaction mixture showed 85.3% 2-(2,4-dihydroxyphenyl)-4,6-bis(2,4-dimethylphenyl)-1,3,5-triazine, 12.8% 2,4,6-tris(2,4-dimethylphenyl)-1,3,5-triazine, and 1.7% unreacted 2-chloro-4,6-bis(2,4-dimethylphenyl)-1,3,5-triazine.

Example 19

Synthesis of 2-(2,4-dihydroxyphenyl)-4,6-bis(2,4-dimethylphenyl)-1,3,5-triazine using 3 eq AlCl$_3$ with 6.5% concentrated HCl To a stirring mixture of 1 eq of cyanuric chloride, 3 eq of AlCl$_3$ in chlorobenzene, was added 6.5% (based on the weight of cyanuric chloride) of concentrated HCl at ice-bath temperature. Within 1.5 h, the HPLC analysis showed almost complete conversion of cyanuric chloride to 2-chloro-4,6-bis(2,4-dimethylphenyl)-1,3,5-triazine and 2,4,6-(2,4-dimethylphenyl)-1,3,5-triazine, which were formed in a ratio of 91:9. Thereafter; the reaction mixture was allowed to react with 1.1 eq of resorcinol and subsequently heated at 85° C. for 1 h. HPLC analysis showed the formation of 83.3% 2-(2,4-dihydroxyphenyl)-4,6-bis(2,4-dimethylphenyl)-1,3,5-triazine, 14.9% 2,4,6-tris(2,4-dimethylphenyl)-1,3,5-triazine, and 1.7% unreacted 2-chloro-4,6-bis(2,4-dimethylphenyl)-1,3,5-triazine. No trisresorcinol-triazine or bisresorcinol-triazine products were detected.

Example 20

Synthesis of 2-(2,4-dihydroxyphenyl)-4,6-bis(2,4-dimethylphenyl)-1,3,5-triazine using 3 eq $AlCl_3$ with 13% concentrated HCl To a stirring mixture of 1 eq of cyanuric chloride, 3 eq of $AlCl_3$, and 1.9 eq of m-xylene in chlorobenzene, was added 13% (based on the weight of cyanuric chloride) of concentrated HCl at ice-bath temperature. Within 30 min at room temperature, 97% of the cyanuric chloride had reacted, to produce 2-chloro-4,6-bis(2,4-dimethylphenyl)-1,3,5-triazine and 2,4,6-tris(2,4-dimethylphenyl)-1,3,5-triazine in a ratio of 96:4; no side products were detected. Further stirring gave 99.5% cyanuric chloride conversion, with the ratio of 2-chloro-4,6-bis(2,4-dimethylphenyl)-1,3,5-triazine to 2,4,6-tris(2,4-dimethylphenyl)-1,3,5-triazine unchanged and no other products were detected. Thereafter, the reaction mixture was allowed to react with 1.1 eq of resorcinol at 85° C. for 1.5 h. HPLC analysis of the reaction mixture showed the formation of 92.7% 2-(2,4-dihydroxyphenyl)-4,6-bis(2,4-dimethylphenyl)-1,3,5-triazine, 5% 2,4,6-tris(2,4-dimethylphenyl)-1,3,5-triazine, and 2.3% unreacted 2-chloro-4,6-bis(2,4-dimethylphenyl)-1,3,5-triazine.

The product was isolated by treating the reaction mixture with cold 2% aqueous HCl. Precipitate was collected by filtration, washed with water, and dried to give 92% yield of crude 2-(2,4-dihydroxyphenyl)-4,6-bis(2,4-dimethylphenyl)-1,3,5-triazine. The actual yield should be even higher than 92%, since some of the product was lost during the sampling for a number of HPLC analyses done during the course of the reaction HPLC analysis of the isolated crude 2-(2,4-dihydroxyphenyl)-4,6-bis(2,4-dimethylphenyl)-1,3,5-triazine showed 92.4% 2-(2,4-dihydroxyphenyl)-4,6-bis(2,4-dimethylphenyl)-1,3,5-triazine, 5% 2,4,6-tris(2,4-dimethylphenyl)-1,3,5-triazine, 2.35% unreacted 2-chloro-4,6-bis(2,4-dimethylphenyl)-1,3,5-triazine, and 0.25% 2,4,6-tris(2,4-dihydroxyphenyl)-1,3,5-triazine.

Example 21

Synthesis of 2-chloro-4,6-bis(2,4-dimethylphenyl)-1,3,5-triazine using 3 eq $AlCl_3$ with 13% concentrated HCl To a stirring mixture of 1 eq of cyanuric chloride, 3 eq of $AlCl_3$ in chlorobenzene, was added 13% (based on the weight of cyanuric chloride) of concentrated HCl at ice-bath temperature After addition of 1.9 eq of m-xylene and the reaction of cyanuric chloride with m-xylene was complete, as indicated by the absence of m-xylene, by HPLC analysis, the reaction mixture was quenched with ice-cold 2% aqueous HCl at about 5° C. The reaction mixture was then extracted with methylene chloride. The organic layer was washed with water, dried over anhydrous sodium sulfate, and the solvent removed under reduced pressure to give a white solid (quantitative yield based on m-xylene, and 95% yield based on cyanuric chloride) HPLC analysis indicated the isolated white solid to consist of >96% pure 2-chloro-4,6-bis(2,4-dimethylphenyl)-1,3,5-triazine.

Example 22

Synthesis of 2-chloro-4,6-bis(2,4-dimethylphenyl)-1,3,5-triazine using 2.5 eq $AlCl_3$ with 13% concentrated HCl To a stirring mixture of 1 eq of cyanuric chloride, 2.5 eq of $AlCl_3$ in chlorobenzene, was added 13% (based on the weight of cyanuric chloride) of concentrated HCl at ice-bath temperature HPLC analysis after 1 h at room temperature showed 89% cyanuric chloride conversion to 2-chloro-4,6-bis(2,4-dimethylphenyl)-1,3,5-triazine and 2,4,6-tris(2,4-dimethylphenyl)-1,3,5-triazine, in a ratio of 82:18. The reaction mixture was left stirring at room temperature overnight after which the complete conversion of cyanuric chloride was detected. The next sample analyzed by HPLC after 22 h at room temperature showed 94% cyanuric chloride conversion, and the ratio of 2-chloro-4,6-bis(2,4-dimethylphenyl)-1,3,5-triazine to 2,4,6-tris(2,4-dimethylphenyl) 1,3,5-triazine to be 43:57.

Example 23

Synthesis of 2-(2,4-dihydroxyphenyl)-4,6-bis(2,4-dimethylphenyl)-1,3,5-triazine using 2.5 eq $AlCl_3$ with 6.5% concentrated HCl To a stirring mixture of 1 eq of cyanuric chloride, 2.5 eq of $AlCl_3$ in chlorobenzene, was added 6.5% (based on the weight of cyanuric chloride) of concentrated HCl at ice-bath temperature. After 22 h at room temperature, 98% of the cyanuric chloride had reacted to give 2-chloro-4,6-bis(2,4-dimethylphenyl)-1,3,5-triazine and 2,4,6-tris(2,4-dimethylphenyl)-1,3,5-triazine, which were present in a ratio of 9:10. The reaction mixture was allowed to react with 1.1 eq of resorcinol and subsequently heated to 85° C. for, 1.5 h. HPLC analysis of the reaction mixture showed 85.4% 2-(2,4-dihydroxyphenyl)-4,6-bis(2,4-dimethylphenyl)-1,3,5-triazine, 11.4% 2,4,6-tris(2,4-dimethylphenyl)-1,3,5-triazine, 2.6% unreacted 2-chloro-4,6-bis(2,4-dimethylphenyl)-1,3,5-triazine, and 0.6% 2,4,6-tris(2,4-dihydroxyphenyl)-1,3,5-triazine.

Example 24

Synthesis of 2-chloro-4,6-bistetralin-1,3,5-triazine

To a stirring mixture of 1 eq of cyanuric chloride (5 g, 0.027 mol) in chlorobenzene, maintained at ice bath temperature under nitrogen, was added 3 eq of $AlCl_3$ (10.87 g, 0.081 mol) over 5-10 min, followed by the addition of conc. HCl (0.54 mL, 0.0065 mol) over 5-10 min, taking care that the reaction temperature did not exceed 5° C. The reaction slurry was stirred at 0-5° C. for another 10 min. The reaction was cooled to −10° C. and tetralin (7.01 mL, 0.0516 mol) was added at −10° C. over 2 h. At the completion of the tetralin addition, the reaction mixture was stirred at −10° C. for 2 h. The reaction was warmed to 0° C. and stirred for 1 h. HPLC analysis of the reaction mixture showed 98.5% conversion of cyanuric chloride to 2-chloro-4,6-bistetralin-1,3,5-triazine and 2,4,6-tristetralin-1,3,5-triazine in a 92:8 ratio. The slurry was warmed to 40° C. and resorcinol (3.29 g, 0.0298 mol) was added and the reaction mixture was stirred at 80° C. for 2 h.

Comparative Example 24

Synthesis of 2-chloro-4,6-bistetralin-1,3,5-triazine

To a stirring mixture of 1 eq of cyanuric chloride (5 g, 0.027 mol) in chlorobenzene (50 mL), maintained at ice bath temperature under nitrogen, was added 3 eq of $AlCl_3$ (10.87 g, 0.081 mol) over 5-10 min. The reaction slurry was stirred at 0-5° C. for another 10 min. The reaction was cooled to −10° C. and tetralin (7.01 mL, 0.0516 mol) was added at −10° C. over 2 h. At the completion of the tetralin addition, the reaction mixture was stirred at −10° C. for 2 h. The reaction was warmed to 0° C. and stirred for 1 h. HPLC analysis of the reaction mixture showed no reaction of cyanuric chloride, and no formation of 2-chloro-4,6-bistetralin-1,3,5-triazine.

Example 25

Synthesis of 2-chloro-4,6-bis(2,4-dimethylphenyl)-1,3,5-triazine using 3 eq $AlCl_3$ with concentrated sulfuric acid To a stirring mixture of 1 eq of cyanuric chloride, 3 eq of $AlCl_3$ in chlorobenzene, was added 0.24 eq of concentrated $H_2SO_4$ at ice-bath temperature. After 5 min of stirring 2 eq of m-xylene was added. After another 5 min, the cooling bath was removed and the reaction mixture was stirred at room temperature WIC analysis after 2 h at room temperature showed 100% of the cyanuric chloride had reacted to give 2-chloro-4,6-bis(2,4-dimethylphenyl)-1,3,5-triazine and 2,4,6-tris(2,4-dimethylphenyl)-1,3,5-triazine, which were present in a ratio of 86:14.

Example 26

Synthesis of 2-(2,4-dihydroxyphenyl)-4,6-bis(2,4-dimethylphenyl)-1,3,5-triazine using 3.5 eq $AlCl_3$ with 10% aqueous sulfuric acid To a stirring mixture of 1 eq of cyanuric chloride, 3.5 eq of $AlCl_3$ in chlorobenzene, was added 0.036 eq of sulfuric acid as a 10% aq. solution at ice-bath temperature. After 10 min of stirring 1.9 eq of m-xylene was added. After 5 min at ice bath temperature the reaction mixture was allowed to warm to 10° C. After 1 h 20 min HPLC analysis showed 89% of the cyanuric chloride had reacted to give 2-chloro-4,6-bis(2,4-dimethylphenyl)-1,3,5-triazine and 2,4,6-tris(2,4-dimethylphenyl)-1,3,5-triazine, which were present in a ratio of 89:11 HPLC analysis, after 3 h at 9-11° C., showed 94% of the cyanuric chloride had reacted to give 2-chloro-4,6-bis(2,4-dimethylphenyl)-1,3,5-triazine and 2,4,6-tris(2,4-dimethylphenyl)-1,3,5-triazine, which were present in a ratio of 95:5. HPLC analysis, after 5 h at 9-11° C. and 17 h at room temperature, showed 98.5% of the cyanuric chloride had reacted to give 2-chloro-4,6-bis(2,4-dimethylphenyl)-1,3,5-triazine and 2,4,6-tris(2,4-dimethylphenyl)-1,3,5-triazine, which were present in a ratio of 97:3.

The reaction mixture was allowed to react with 1.1 eq of resorcinol and subsequently heated to 85° C. for 3 h. HPLC analysis of the reaction mixture showed 92.7% 2-(2,4-dihydroxyphenyl)-4,6-bis(2,4-dimethylphenyl)-1,3,5-triazine, 4% 2,4,6-tris(2,4-dimethylphenyl)-1,3,5-triazine, 2.4% unreacted 2-chloro-4,6-bis(2,4-dimethylphenyl)-1,3,5-triazine, and 0.9% 2,4,6-(2,4-dihydroxyphenyl)-1,3,5-triazine.

Example 27

Synthesis of 2-chloro-4,6-bis(2,4-dimethylphenyl)-1,3,5-triazine using 3 eq $AlCl_3$ with benzoic acid To a stirring mixture of 1 eq of cyanuric chloride, 3 eq of $AlCl_3$ in chlorobenzene, was added 0.24 eq of benzoic acid as a 4% solution in chlorobenzene at ice-bath temperature. m-Xylene (1.95 eq) was then added. After 5 min at ice bath temperature, the reaction was allowed to warm to room temperature. HPLC analysis after 22 h at room temperature, showed 99.5% of the cyanuric chloride had reacted to give 2-chloro-4,6-bis(2,4-dimethylphenyl)-1,3,5-triazine and 2,4,6-tris(2,4-dimethylphenyl)-1,3,5-triazine, which were present in a ratio of 82:18.

Example 28

Synthesis of 2-(2,4-dihydroxyphenyl)-4,6-bis(2,4-dimethylphenyl)-1,3,5-triazine using 3 eq $AlCl_3$ and 6.5% concentrated HCl To a stirring mixture of 1 eq of cyanuric chloride, 3 eq of $AlCl_3$ in chlorobenzene, was added 0.24 eq of concentrated HCl at ice-bath temperature. After 45 min, 0.95 eq of m-xylene and 0.95 eq of toluene were added. After 45 min at ice bath temperature the reaction was stirred at 9° C. for 1 h and then at room temperature for 2 h. HPLC analysis showed 2-chloro-4,6-bis(2,4-dimethylphenyl)-1,3,5-triazine as the major product with lesser amounts of 2-chloro-4,6-bis(4-methylphenyl)-1,3,5-triazine, and 2-chloro-4-(4-methylphenyl)-6-(2,4-dimethylphenyl)-1,3,5-triazine.

The reaction mixture was allowed to react with 1.1 eq of resorcinol and subsequently heated to 85° C. for 2 h HPLC analysis of the reaction mixture showed 2-(2,4-dihydroxyphenyl)-4,6-bis(2,4-dimethylphenyl)-1,3,5-triazine as the major product with lesser amounts of 2-(2,4-dihydroxyphenyl)-4,6-bis(4-methylphenyl)-1,3,5-triazine, and 2-(2,4-dihydroxyphenyl)-4-(4-methylphenyl)-6-(2,4-dimethylphenyl)-1,3,5-triazine.

Example 29

Synthesis of 2-(2,4-dimethoxyphenyl)-4,6-bis(2,4-dimethylphenyl)-1,3,5-triazine using 3 eq $AlCl_3$ with concentrated HCl To a stirring mixture of 1 eq of cyanuric chloride, 3 eq of $AlCl_3$ in chlorobenzene, was added 0.24 eq of concentrated HCl at ice-bath temperature. After 10 min, 1.9 eq of m-xylene was added. The reaction was stirred at ice bath temperature for 2 h and then at room temperature for 5 h. HPLC analysis showed formation of 2-chloro-4,6-bis(2,4-dimethylphenyl)-1,3,5-triazine as the major product and 2,4,6-tris(2,4-dimethylphenyl)-1,3,5-triazine in a 91:9 ratio. The reaction mixture was allowed to react with 1.1 eq of 1,3-dimethoxybenzene. The mixture was heated to 59-61° C. and stirred for 2 h, then heated 85° C. and stirred for 5 h. HPLC analysis of the reaction mixture showed 76% 2-(2,4-dimethoxyphenyl)-4,6-bis(2,4-dimethylphenyl)-1,3,5-triazine and 24% 2,4,6-tris(2,4-dimethylphenyl)-1,3,5-triazine (HPLC area percent at 290 nm) as the only products.

Example 30

Synthesis of 2-chloro-4,6-bis(2,4-dimethylphenyl)-1,3,5-triazine using 2.5 eq $AlCl_3$, and 0.12 eq anhydrous HCl To a mixture of cyanuric chloride in chlorobenzene cooled to 5° C. was added 2.5 eq of $AlCl_3$, 0.12 eq of anhydrous HCl (as a 0.28 N solution in chlorobenzene), and 1.9 eq of m-xylene. This mixture was warmed to 23° C. with stirring, and the progress of the reaction as monitored by HPLC. The data are given in Table I below.

TABLE I

Reaction Profile for Anhydrous HCl

| Time (h) | Cyanuric chloride Conversion (%) | Mono-xylyl-Bis-chloro-Triazine | Bis-xylyl-monochloro-triazine | Tris-xylyl-Triazine |
| --- | --- | --- | --- | --- |
| 1 | 3 | 100 | | |
| 2 | 6 | 100 | | |
| 3 | 9 | 100 | | |
| 25 | 65 | 58 | 40 | 2 |

The cyanuric chloride conversion is based on area percent at 210 nm. The amounts of the other components are based on area percent at 290 nm.

Example 31

Synthesis of 2-chloro-4,6-bis(2,4-dimethylphenyl)-1,3,5-tetrazine using 3 eq $AlCl_3$ and 0.2 eq anhydrous HCl To a mixture of cyanuric chloride in chlorobenzene cooled to 5° C. was added 3 eq of $AlCl_3$, 0.2 eq of anhydrous HCl (as a 0.156 N solution in chlorobenzene), and 1.9 eq of m-xylene. This mixture was then warmed to 23° C. with stirring and the progress of the reaction was monitored by HPLC The data are given in Table II below.

TABLE II

Reaction Profile for Anhydrous HCl (0.20 eq)

| Time (h) | Cyanuric Chloride Conversion (%) | Monoxylyl-bischloro-triazine | Bis-xylyl-monochloro-triazine | Tris-xylyl-triazine | Bisxylyl-monochloro:Tris-xylyl* |
| --- | --- | --- | --- | --- | --- |
| 1 | 2 | 100 | | | |
| 2.5 | 6 | 100 | | | |
| 4 | 15 | 97 | 3 | | |
| 5.5 | 19 | 97 | 3 | | |
| 23 | 59 | 89 | 10 | 1 | 94:6 |
| 48 | 88 | 0.5 | 65.5 | 34 | 78:22 |

*corrected ratio.

Example 32

Synthesis of 2-(2,4-dihydroxyphenyl)-4,6-bis(2,4-dimethylphenyl)-1,3,5-triazine using 0.2 eq resorcinol and 3 eq $AlCl_3$ with 0.55 eq $H_2O$ To a stirring mixture of 1 eq of cyanuric chloride, 3 eq of $AlCl_3$ and 0.2 eq of resorcinol in chlorobenzene, was added 0.55 eq of water at ice-bath temperature. An immediate reaction with $AlCl_3$ was observed. After 10 min of stirring, 1.9 eq of m-xylene was added. After another 10 min, the cooling bath was removed and the reaction mixture was stirred at room temperature. HPLC analysis of the reaction mixture after 1.5 h at room temperature showed 84% cyanuric chloride conversion to 2-chloro-4,6-bis(2,4-dimethylphenyl)-1,3,5-triazine and 2,4,6-tris(2,4-dimethylphenyl)-1,3,5-triazine, in a 95:5 ratio respectively. After 2.5 h at room temperature HPLC analysis showed 95% conversion of cyanuric chloride, and a ratio of 2-chloro-4,6-bis(2,4-dimethylphenyl)-1,3,5-triazine to 2,4,6-tris(2,4-dimethylphenyl)-1,3,5-triazine of 94:6. Thereafter, 1 eq of resorcinol was added and the reaction mixture was stirred at 85° C. for 1 h. HPLC analysis of the reaction mixture showed 89.4% 2-(2,4-dihydroxyphenyl)-4,6-bis(2,4-dimethylphenyl)-1,3,5-triazine, 7.7% 2,4,6-tris(2,4-dimethylphenyl)-1,3,5-triazine, 1.6% unreacted 2-chloro-4,6-bis(2,4-dimethylphenyl)-1,3,5-triazine and 1.3% 2,4,6-tris(2,4-dihydroxyphenyl)-1,3,5-triazine.

Example 33

Synthesis of 2-(2,4-dihydroxyphenyl)-4,6-bis 2,4-dimethylphenyl)-1,3,5-triazine using 3 eq $AlCl_3$ with 0.55 eq water To a stirring mixture of 1 eq of cyanuric chloride, 3 eq of $AlCl_3$ in chlorobenzene, was added 0.55 eq of water at ice-bath temperature. After 10 min 1.9 eq of m-xylene was added. HPLC analysis after 30 min at room temperature showed 93% cyanuric chloride conversion to 2-chloro-4,6-bis(2,4-dimethylphenyl)-1,3,5-triazine and 2,4,6-tris(2,4-dimethylphenyl)-1,3,5-triazine, in a ratio of 94:6 respectively. After 1 h at room temperature HPLC analysis showed 98% cyanuric chloride conversion to 2-chloro-4,6-bis(2,4-dimethylphenyl)-1,3,5-triazine and 2,4,6-tris(2,4-dimethylphenyl)-1,3,5-triazine, in a ratio of 92:8. After 4.5 h at room temperature, HPLC analysis showed conversion of cyanuric chloride had increased to 99%, and the ratio of 2-chloro-4,6-bis(2,4-dimethylphenyl)-1,3,5-triazine to 2,4,6-tris(2,4-dimethylphenyl)-1,3,5-triazine was 93:7.

Thereafter, 1.1 eq of resorcinol was added and the mixture stirred at 85° C. for 2 h HPLC analysis of the reaction mixture showed 91.1% 2-(2,4-dihydroxyphenyl)-4,6-bis(2,4-dimethylphenyl)-1,3,5-triazine, 6.3% 2,4,6-tris(2,4-dimethylphenyl)-1,3,5-triazine, 1.8% unreacted 2-chloro-4,6-bis(2,4-dimethylphenyl)-1,3,5-triazine, and 0.75% 2,4,6-tris(2,4-dihydroxyphenyl)-1,3,5-triazine.

Example 34

Synthesis of 2-chloro-4,6-bis(2,4-dimethylphenyl)-1,3,5-triazine using 2.5 eq $AlCl_3$ with 0.55 eq water To a stirring mixture of 1 eq of cyanuric chloride, 2.5 eq of $AlCl_3$ in chlorobenzene, was added 0.55 eq of water at ice-bath temperature. Analysis by HPLC, after 30 min at room temperature, showed 92% conversion of cyanuric chloride to 2-chloro-4,6-bis(2,4-dimethylphenyl)-1,3,5-triazine and 2,4,6-tris(2,4-dimethylphenyl)-1,3,5-triazine, in a ratio of 94:6. After 1 h at room temperature, HPLC analysis of the reaction mixture showed 96% conversion of cyanuric chloride, and a ratio of 2-chloro-4,6-bis(2,4-dimethylphenyl)-1,3,5-triazine to 2,4,6-tris(2,4-dimethylphenyl)-1,3,5-triazine of 88:12. After 4.5 h at room temperature, HPLC analysis showed 97% conversion of cyanuric chloride and a ratio of 2-chloro-4,6-bis(2,4-dimethylphenyl)-1,3,5-triazine to 2,4,6-tris(2,4-dimethylphenyl)-1,3,5-triazine of 77:23.

Example 35

Synthesis of 2-chloro-4,6-bis(2,4-dimethylphenyl)-1,3,5-triazine using 23.25 eq $AlCl_3$ with 0.55 eq water To a stirring mixture of 1 eq of cyanuric chloride, 3.25 eq of $AlCl_3$ in chlorobenzene, was added 0.55 eq of water at ice-bath temperature. After 10 min 1.9 eq of m-xylene was added. Within 1 h, 98% conversion of cyanuric chloride was detected, based on HPLC analysis. The ratio of 2-chloro-4,6-bis(2,4-dimethylphenyl)-1,3,5-triazine to 2,4,6-tris(2,4-dimethylphenyl)-1,3,5-triazine was 92:8. A final sample analysis after complete disappearance of m-xylene showed 99% cyanuric chloride conversion, and the ratio of the products, 2-chloro-4,6-bis(2,4-dimethylphenyl)-1,3,5-triazine to 2,4,6-tris(2,4-dimethylphenyl)-1,3,5-triazine, was 89:11.

Example 36

Synthesis of 2-chloro-4,6-bis(2,4-dimethylphenyl)-1,3,5-triazine using 3 eq $AlCl_3$ without promoter To a stirring mixture of 1 eq of cyanuric chloride, 3 eq of $AlCl_3$ in chlorobenzene was added. After 10 min 1.9 eq of m-xylene was added HPLC analysis after 2 h showed 5% cyanuric chloride conversion to 2,4-dichloro-6-(2,4-dimethylphenyl)-1,3,5-triazine. After 24 h at room temperature HPLC analysis showed 46% cyanuric chloride conversion to 2,4-dichloro-6-(2,4-dimethylphenyl)-1,3,5-triazine and 2-chloro-4,6-bis(2,4-dimethylphenyl)-1,3,5-triazine in a 96:4.

Example 37

Synthesis of 2-chloro-4,6-bis(2,4-dimethylphenyl)-1,3,5-triazine using 3.25 eq $AlCl_3$ without promoter The cyanuric chloride was allowed to react with 2 eq of m-xylene in the presence of 3.25 eq of $AlCl_3$ in chlorobenzene at 5° C. for 0.5 h and then at room temperature for 3 h. HPLC analysis. After 4 h, showed about 15% cyanuric chloride conversion to 2,4-dichloro-6-(2,4-dimethylphenyl)-1,3,5-triazine; no 2-chloro-4,6-bis(2,4-dimethylphenyl)-1,3,5-triazine or 2,4,6-tris(2,4-dimethylphenyl)-1,3,5-triazine was detected. After 24 h at room temperature, HPLC analysis showed about 51% conversion of cyanuric chloride to 2,4-dichloro-6-(2,4-dimethylphenyl)-1,3,5-triazine and 2-chloro-4,6-tris(2,4-dimethylphenyl)-1,3,5-triazine, formed in a 91:9 ratio.

Example 38

Synthesis of 2-chloro-4,6-bis(2,4-dimethylphenyl)-1,3,5-triazine using 3.5 eq $AlCl_3$ without promoter The cyanuric chloride was allowed to react with 2 eq of m-xylene in the presence of 3.5 eq of $AlCl_3$ in chlorobenzene at 5° C. for 0.5 h and then at room temperature for 3 h HPLC analysis. After 4 h, showed about 6% cyanuric chloride conversion to 2,4-dichloro-6-(2,4-dimethylphenyl)-1,3,5-triazine; no 2-chloro-4,6-bis(2,4-dimethylphenyl)-1,3,5-triazine or 2,4,6-tris(2,4-dimethylphenyl)-1,3,5-triazine was detected. After 24 h at room temperature, HPLC analysis showed about 38% conversion of cyanuric chloride to 2,4-dichloro-6-(2,4-dimethylphenyl)-1,3,5-triazine and 2-chloro-4,6-bis(2,4-dimethylphenyl)-1,3,5-triazine, formed in a 96:4 ratio.

Example 39

Preparation of 2-(2,4-dihydroxyphenyl)-4,6-bis(2,4-dimethylphenyl)-1,3,5-triazine with dichloromethane and 2.5 eq $AlCl_3$ To a stirring mixture of 1 eq of cyanuric chloride 0.4 eq of dichloromethane in chlorobenzene was added 2.5 eq of aluminum chloride at ice-bath temperature, the cooling bath was removed and the reaction mixture stirred at room temperature. The HPLC analysis after 3 h at room temperature showed 14% of cyanuric chloride conversion to 2,4-dichloro-6-(2,4-dimethylphenyl)-1,3,5-triazine and 2-chloro-4,6-bis(2,4-dimethylphenyl)-1,3,5-triazine formed in a ratio of 93:7. After about 14 h at room temperature, HPLC analysis showed 98.5% cyanuric chloride conversion to 2-chloro-4,6-bis(2,4-dimethylphenyl)-1,3,5-triazine and 2,4,6-tris(2,4-dimethylphenyl)-1,3,5-triazine in a ratio of 87:13.

To the above reaction mixture, 1 eq of resorcinol was added and the mixture stirred at 80-85° C. for 1 h. HPLC analysis of the reaction mixture showed 76% of 2-(2,4-dihydroxyphenyl)-4,6-bis(2,4-dimethylphenyl)-1,3,5-triazine and 14% of 2,4,6-tris(2,4-dimethylphenyl)-1,3,5-triazine.

Example 40

Preparation of 2-(2,4-dihydroxyphenyl)-4,6-bis(2,4-dimethylphenyl)-1,3,5-triazine with dichloromethane, resorcinol and 2.5 eq aluminum chloride To a stirring mixture of 1 eq of cyanuric chloride, 0.4 eq of dichloromethane, and 0.2 eq of resorcinol in chlorobenzene, was added 2.5 eq of aluminum chloride at ice-bath temperature, the cooling bath was removed and the reaction mixture stirred at room temperature. After 15 min, 10.9 eq of m-xylene was added and after 15 min of stirring at ice-bath temperature, the cooling bath was removed and the reaction mixture stirred at room temperature. HPLC, analysis after 3 h at room temperature showed 95% of cyanuric chloride conversion to 2-chloro-4,6 bis(2,4-dimethylphenyl)-1,3,5-triazine and 2,4,6-tris(2,4-dimethylphenyl)-1,3,5-triazine formed in a ratio of 92:8.

To the above reaction mixture, 1 eq of resorcinol was added and the mixture stirred at 80-85° C. for 1.5 h. HPLC analysis of the reaction mixture showed 80.5% of 2-(2,4-dihydroxyphenyl)-4,6-bis(2,4-dimethylphenyl)-1,3,5-triazine and 9.9% of 2,4,6-tris(2,4-dimethylphenyl)-1,3,5-triazine.

Example 41

Preparation of 2-(2,4-dihydroxyphenyl)-4,6-bis(2,4-dimethylphenyl)-1,3,5-triazine with 2.3 eq of tert-butyl chloride and 2.5 eq aluminum chloride To a stirring mixture of 1 eq of cyanuric chloride and 2.5 eq of aluminum chloride in chlorobenzene at ice bath temperature was added 2.3 eq of tert-butyl chloride over 1 h. After 5 min of stilling, 1.95 eq of m-xylene was added over 5 min. The ice bath was replaced with a water bath, and the reaction mixture was allowed to warmed to room temperature. After 5 min at room temperature, HPLC analysis showed 97% of cyanuric chloride conversion to 2-chloro-4,6-bis(2,4-dimethylphenyl)-1,3,5-triazine and 2,4,6-tris(2,4-dimethylphenyl) 1,3,5-triazine, present in a ratio of 98:2, To the above reaction was added 1.1 eq of resorcinol, and the mixture stirred at 80° C. for 3 h HPLC analysis of the reaction mixture showed 94% of 2-(2,4-dihydroxyphenyl)-4,6 bis(2,4-dimethylphenyl)-1,3-triazine, 3.5% of 2,4,6-tris(2,4-dimethylphenyl)-1,3,5-triazine, 2.5% of unreacted 2-chloro-4,6-bis(2,4-dimethylphenyl)-1,3,5-triazine.

Example 42

Preparation of 2-chloro-4,6-bis(2,4-dimethylphenyl)-1,3,5-triazine with 0.46 eq of tert-butyl chloride with 2.5 eq aluminum chloride To a stirring mixture of 1 eq of cyanuric chloride and 2.5 eq of aluminum chloride in chlorobenzene at ice bath temperature was added 0.46 eq of tert-butyl chloride over 10 min. After 5 min. of stirring, 10.95 eq of m-xylene was added over 5 min. After 5 min, the ice bath was replaced with a water bath, and the reaction mixture warmed to room temperature After stirring at room temperature for 22 h, HPLC analysis showed 98% of cyanuric chloride conversion to 2-chloro-4,6-bis(2,4-dimethylphenyl)-1,3,5-triazine and 2,4,6-tris (2,4-dimethylphenyl)-1,3,5-triazine, present in a ratio of 84:16.

Example 43

Preparation of 2-(2,4-dihydroxyphenyl)-4,6-bis(2,4-dimethylphenyl)-1,3,5-triazine with 0.5 eq tert-butyl-chloride 0.2 resorcinol and 2.5 eq aluminum chloride To a stirring mixture of 1 eq of cyanuric chloride 0.2 eq of resorcinol, and 2.5 eq of aluminum chloride in chlorobenzene at ice bath temperature was added 0.5 eq of tert-butyl chloride over 10 min. After 5 min. of stirring, 1.95 eq of m-xylene was added. The ice bath was replaced with a water bath, and the reaction mixture was allowed to warm to room temperature. After stirring at room temperature for 2 h, HPLC analysis showed 97% of cyanuric chloride conversion to 2-chloro-4,6-bis(2,4-dimethylphenyl)-1,3,5-triazine and 2,4,6-tris(2,4-dimethylphenyl)-1,3,5-triazine, present in a ratio of 91:9.

To the above reaction mixture was added 1 eq of resorcinol, and the mixture stirred at 78-82° C. for 3 h. HPLC analysis of the reaction mixture showed 86% of 2-(2,4-dihydroxyphenyl)-4,6-bis(2,4-dimethylphenyl)-1,3,5-triazine, 12% of 2,4,6-tris(2,4-dimethylphenyl)-1,3,5-triazine, 2% of unreacted 2-chloro-4,6-bis(2,4-dimethylphenyl)-1,3,5-triazine.

Example 44

Synthesis of 2-(2,4-dihydroxyphenyl)-4,6-bis(2,4-dimethylphenyl)-1,3,5-triazine using sodium hydroxide and 3 eq of aluminum chloride To a stirring mixture of 3.7 g (1 eq) of cyanuric chloride, 8 g (3 eq) of aluminum chloride in 50 mL chlorobenzene, was added 0.4 mL of aqueous sodium hydroxide solution (50%) at ice-bath temperature. After 10 min of stirring, 1.9 eq of m-xylene was added. The cooling bath was removed and the reaction mixture stirred at room temperature HPLC analysis after 30 min at room temperature showed 91% of cyanuric chloride conversion to 2-chloro-4,6-bis(2,4-dimethylphenyl)-1,3,5-triazine and 2,4,6-tris(2,4-dimethylphenyl)-1,3,5-triazine, formed in a ratio of 96:4 A second sample analyzed after 1 h at room temperature showed 94% of cyanuric chloride conversion to 2-chloro-4,6-bis(2,4-dimethylphenyl)-1,3,5-triazine and 2,4,6-tris(2,4-dimethylphenyl)-1,3,5-triazine, in a ratio of 92:8. After a total of 4 h at room temperature, HPLC analysis showed 95% conversion of cyanuric chloride and a ratio of 2-chloro-4,6-bis(2,4-dimethylphenyl)-1,3,5-triazine to 2,4,6-tris(2,4-dimethylphenyl)-1,3,5-triazine of 89:11.

To the above reaction mixture, 1.1 eq of resorcinol was added and the mixture heated with stirring at 80° C. for 2 h. HPLC analysis of the reaction mixture showed 80% of 2-(2,4-dihydroxyphenyl)-4,6-bis(2,4-dimethylphenyl)-1,3,5-triazine, 16% of 2,4,6-tris(2,4-dimethylphenyl)-1,3,5-triazine, 1.5% unreacted 2-chloro-4,6-bis(2,4-dimethylphenyl)-1,3,5-triazine and 2.2% of 2,4,6-tris(2,4-dihydroxylphenyl)-1,3,5-triazine.

Example 45

Synthesis of 2-(2,4-dihydroxyphenyl)-4,6-bis(2,4-dimethylphenyl)-1,3,5-triazine using aluminum hydroxide with 3 eq aluminum chloride To a stirring mixture of 3.7 g (1 eq) of cyanuric chloride, 8 g (3 eq) of aluminum chloride in 50 mL chlorobenzene was added 0.39 g (0.5 eq) of aluminum hydroxide at ice-bath temperature. After 10 min of stirring, 1.9 eq of m-xylene was added. The cooling bath was removed after 10 min and the reaction mixture stirred at room temperature. HPLC analysis after 20 h at room temperature showed 98% of cyanuric chloride conversion to 2-chloro-4,6-bis(2,4-dimethylphenyl)-1,3,5-triazine and 2,4,6-tris(2,4-dimethylphenyl)-1,3,5-triazine, formed in a ratio of 80:20.

To the above reaction mixture, 1.1 eq of resorcinol was added and the mixture heated with stirring at 80° C. for 2 h. HPLC analysis of the reaction mixture showed 74% of 2-(2,4-dihydroxyphenyl)-4,6-bis(2,4-dimethylphenyl)-1,3,5-triazine, 22% of 2,4,6-tris(2,4-dimethylphenyl)-1,3,5-triazine, 1.5% of unreacted 2-chloro-4,6-bis(2,4-dimethylphenyl)-1,3,5-triazine, and 1.4% of 2,4,6-tris(2,4-dihydroxylphenyl)-1,3,5-triazine.

Example 46

Synthesis of 2-(2,4-dihydroxyphenyl)-4,6-bis(2,4-dimethylphenyl)-1,3,5-triazine using aq. ammonium hydroxide with 3 eq aluminum chloride To a stirring mixture of 1 eq of cyanuric chloride and 3 eq of aluminum chloride in chlorobenzene at ice bath temperature was added 0.38 eq of aq. ammonium hydroxide over 15 min. After 15 min. of stirring, 1.95 eq of m-xylene was added. The ice bath was replaced with a water bath, and the reaction mixture was allowed to warm to room temperature. After 4 h at room temperature, HPLC analysis showed 97% of cyanuric chloride conversion to 2-chloro-4,6-bis(2,4-dimethylphenyl)-1,3,5-triazine and 2,4,6-tris(2,4-dimethylphenyl)-1,3,5-triazine, present in a ratio of 89:11. After an additional 1 h at room temperature, the cyanuric chloride conversion was >99%% and the 2-chloro-4,6-bis(2,4-dimethylphenyl)-1,3,5-triazine to 2,4,6-tris(2,4-dimethylphenyl)-1,3,5-triazine ratio was at 89:11.

To the above reaction mixture was added 1.1 eq of resorcinol, and the mixture stirred at 78-82° C. for 3 h. HPLC analysis of the reaction mixture showed 84% of 2-(2,4-dihydroxylphenyl)-4,6-bis(2,4-dimethylphenyl)1,3,5-triazine, 12% of 2,4,6-tris(2,4-dimethylphenyl)-1,3,5-triazine, and 2% of unreacted 2-chloro-4,6-bis(2,4-dimethylphenyl)-1,3, 5-triazine.

Example 47

Synthesis of 2-(2,4-dihydroxyphenyl)-4,6-bis(2,4-dimethylphenyl)-1,3,5-triazine using sodium methoxide and 3 eq aluminum chloride To a stirring mixture of 3 eq of aluminum chloride in chlorobenzene at ice bath temperature was added 0.5 eq of sodium methoxide over 15 min. The reaction mixture was warmed to room temperature for 0.5 h and then cooled back to ice bath temperature. To the reaction mixture was added 1 eq of cyanuric chloride and 1.95 eq of m-xylene. The ice bach was replaced with a water bath, and the reaction mixture warmed to room temperature. After 7.5 h at room temperature, HPLC analysis showed 98% cyanuric chloride conversion to 2-chloro-4,6-bis(2,4-dimethylphenyl)-1,3,5-triazine and 2,4,6-tris(2,4-dimethylphenyl)-1,3,5-triazine, present in a ratio of 75:25.

To the above reaction mixture was added 1.1 eq of resorcinol, and the mixture stirred at 85° C. for 4 h. HPLC analysis of the reaction mixture showed 80% of 2-(2,4-dihydroxyphenyl)-4,6-bis(2,4-dimethylphenyl)-1,3,5-triazine, 18% of 2,4,6-tris(2,4-dimethylphenyl)-1,3,5-triazine and 2% of unreacted 2-chloro-4,6-bis(2,4-dimethylphenyl)-1,3,5-triazine.

Example 48

Synthesis of 2-chloro-4,6-bis(2,4-dimethylphenyl)-1,3,5-triazine using α-methylstyrene with 3 eq aluminum chloride To a stirring mixture of 1 eq of cyanuric chloride, 3 eq of aluminum chloride in chlorobenzene was added 0.5 eq of α-methylstyrene at ice-bath temperature. After 10 min of stirring, 1.9 eq of m-xylene was added. After another 10 min, the cooling bath was removed and the reaction mixture was stirred at room temperature HPLC analysis after 16 h at room temperature showed 96% of cyanuric chloride conversion to 2-chloro-4,6-bis(2,4-dimethylphenyl)-1,3,5-triazine and 2,4,6-tris(2,4-dimethylphenyl)-1,3,5-triazine (tris-xylyl triazine), formed in a ratio of 73:27.

Example 49

Synthesis of 2-chloro-4,6-bis(2,4-dimethylphenyl)-1,3,5-triazine with 3 eq aluminum chloride without promoter To a stirring mixture of 1 eq of cyanuric chloride, 3 eq of aluminum chloride in chlorobenzene was added at ice-bath temperature. After addition of m-xylene, the reaction mixture was allowed to stir at room temperature for a total of 24 h. HPLC analysis of the reaction mixture showed about 46% cyanuric chloride conversion to 2,4-dichloro-6-(2,4-dimethylphenyl)-1,3,5-triazine and 2-chloro-4,6-bis(2,4-dimethylphenyl)-1,3,5-triazine, formed in a ratio of 96:4.

Example 50

Synthesis of 2-chloro-4,6-bis(2,4-dimethylphenyl)-1,3,5-triazine with butyryl chloride and 3 eq aluminum chloride To a stirring mixture of 1 eq of cyanuric chloride, 3 eq of aluminum chloride in chlorobenzene was added 0.5 eq of butyryl chloride at ice-bath temperature. After 10 min of stirring, 1.9 eq of m-xylene was added. After another 10 min, the cooling bath was removed and the reaction mixture was stirred at room temperature. HPLC analysis after 16 h at room temperature showed 92% of cyanuric chloride conversion to 2-chloro-4,6-bis(2,4-dimethylphenyl)-1,3,5-triazine and 2,4,6-tris(2,4-dimethylphenyl)-1,3,5-triazine, formed in a ratio of 78:22.

Example 51

Synthesis of 2-(2,4-dihydroxyphenyl)-4,6-bis(2,4-dimethylphenyl)-1,3,5-triazine using pyridine hydrochloride with 3.5 eq of aluminum chloride To a stirring mixture of 1 eq of cyanuric chloride and 3.5 eq of aluminum chloride in chlorobenzene was added 0.5 eq of pyridine hydrochloride at ice-bath temperature. After 10 min of stirring, 1.9 eq of m-xylene was added. The reaction mixture was stirred for 1 h at ice bath temperature, 3.5 h at 10° C., and 6.5 h at 15-20° C. HPLC analysis showed 98% of cyanuric chloride conversion to 2-chloro-4,6-bis(2,4-dimethylphenyl)-1,3,5-triazine and 2,4,6-tris(2,4-dimethylphenyl)-1,3,5-triazine, formed in a ratio of 88:12.

To the above reaction mixture was added 1.1 eq of resorcinol, and the mixture stirred at 85° C. for 3 h. HPLC analysis of the reaction mixture showed 86% of 2-(2,4-dihydroxyphenyl)-4,6-bis(2,4-dimethylphenyl)-1,3,5-triazine, 13% of 2,4,6-tris(2,4-dimethylphenyl)-1,3,5-triazine, and 1% of unreacted 2-chloro-4,6-bis(2,4-dimethylphenyl)-1,3,5-triazine.

Example 52

Synthesis of 2-chloro-4,6-bis(2,4-dimethylphenyl)-1,3,5-triazine using 3.5 eq aluminum chloride To a stirring mixture of 1 eq of cyanuric chloride and 3.5 eq of aluminum chloride in chlorobenzene, after 10 min of stirring, 1.9 eq of m-xylene was added. HPLC analysis after 4 h at room temperature showed 6% cyanuric chloride conversion to 2,4-dichloro-6-(2,4-dimethylphenyl)-1,3,5-triazine with no formation of 2-chloro-4,6-bis(2,4-dimethylphenyl)-1,3,5-triazine. The reaction mixture was stirred at room temperature for 24 h. HPLC analysis showed about 38% conversion of cyanuric chloride to 2,4-dichloro-6-(2,4-dimethylphenyl)-1,3,5-triazine and 2-chloro-4,6-bis(2,4-dimethylphenyl)-1,3,5-triazine, in a 96:4 ratio.

Example 53

Synthesis of 2-chloro-4,6-bis(2,4-dimethylphenyl)-1,3,5-triazine using benzyltriethylammonium chloride and resorcinol and 2.5 eq aluminum chloride To a stirring mixture of 1 eq of cyanuric chloride, 0.2 eq benzyltriethylammonium chloride, and 0.2 eq of resorcinol in chlorobenzene was added 2.5 eq of aluminum chloride at ice-bath temperature. After 10 min of stirring, 10.9 eq of m-xylene was added. The reaction mixture was stirred for 1 hour at ice bath temperature, and 3 h at 18-20° C. HPLC analysis showed 72% of cyanuric chloride conversion to 2-chloro-4,6-bis(2,4-dimethylphenyl)-1,3,5-triazine and 2,4,6-tris(2,4-dimethylphenyl)-1,3,5-triazine, in a ratio of 86:14.

Example 54

Synthesis of 2-(2,4-dihydroxyphenyl)-4,6-bis(2,4-dimethylphenyl)-1,3,5-triazine using lithium chloride with 3 eq of aluminum chloride To a stirring mixture of 1 eq of cyanuric chloride and 3 eq of aluminum chloride in chlorobenzene was added 0.5 eq of lithium chloride at ice-bath temperature. After 10 min. of stirring, 1.9 eq of m-xylene was added. The reaction mixture was allowed to stir at room temperature. HPLC analysis of the reaction mixture after 44 h of stirring at room temperature showed 97% cyanuric chloride conversion to 2-chloro-4,6-bis(2,4-dimethylphenyl)-1,3,5-triazine and 2,4,6-tris(2,4-dimethylphenyl)-1,3,5-triazine, in a ratio of 81:19.

To the above reaction mixture, 10.1 eq of resorcinol was added and the mixture stirred at 70° C. for 3 hours. HPLC analysis of the reaction mixture showed 76% of 2-(2,4-dihydroxyphenyl)-4,6-bis(2,4-dimethylphenyl)-1,3,5-triazine, 20% of 2,4,6-tris(2,4-dimethylphenyl)-1,3,5-triazine, 1% of unreacted 2-chloro-4,6-bis(2,4-dimethylphenyl)-1,3,5-triazine, and 2% of 2,4,6-tris(2,4-dihydroxylphenyl)-1,3,5-triazine.

Example 55

Preparation of 2-(2,4-dihydroxyphenyl)-4,6-bis(2,4-dimethylphenyl)-1,3,5-triazine Part A: Preparation of 2-chloro-4,6-bis(2,4-dimethylphenyl)-1,3,5-triazine using 0.50 eq of allyl bromide as promoter To a stirring mixture of 1 eq of cyanuric chloride and 3 eq of aluminum chloride in chlorobenzene at ice bath temperature was added 0.5 eq of allyl bromide over 20 min. An immediate reaction with aluminum chloride was observed during the addition. After 10 min at 0-1° C., 1.9 eq of m-xylene was added over 5 nm. After 30 min at 0-1° C., the ice bath was replaced with a cold-water bath, and the reaction mixture was stirred at 17-19° C. for 25.5 h HPLC analysis showed 95% of cyanuric chloride conversion to 2-chloro-4,6-bis(2,4-dimethylphenyl)-1,3,5-triazine and 2,4,6-tris(2,4-dimethylphenyl)-1,3,5-triazine, present in a ration of 86:14. A small amount of by-product was detected, probably arising from the reaction of 2-chloro-4,6-(2,4-dimethylphenyl)-1,3,5-triazine (CDMPT) with allyl bromide, was observed. If this product is counted along with CDMPT itself, the bis-xylyl-monochloro-triazine to tris-xylyl-triazine ratio increases to 89:11.

Part B: Preparation of 2-(2,4-dihydroxyphenyl)-4,6-bis(2,4-dimethylphenyl)-1,3,5-triazine To the above reaction mixture was added 1:1 eq resorcinol and the mixture was stirred at 85° C. for 17 h. HPLC analysis of the reaction mixture showed 87% 2-(2,4-dihydroxyphenyl)-4,6-bis(2,4-dimethylphenyl)-1,3,5-triazine and 13% 2,4,6-tris(2,4-dimethylphenyl)-1,3,5-triazine.

Example 56

Preparation of 2-(2,4-dihydroxyphenyl)-4,6-bis(2,4-dimethylphenyl)-1,3,5-triazine Part A: Preparation of 2-chloro-4,6-bis(2,4-dimethylphenyl)-1,3,5-triazine; using 0.4 eq. of 3-methyl-2-buten-1-ol as promoter To a stirring mixture of 1 eq of cyanuric chloride and 3 eq of aluminum chloride in chlorobenzene at −13° C. to −15° C. was added 0.4 eq of 3-methyl-2-buten-1-ol over 15 min. An immediate reaction with aluminum chloride was observed during the addition. The mixture was allowed to warm to 0-1° C. and after stirring for 10 min, 1.9 eq of m-xylene was added over 10 min. After stirring for 2 h at 0-1° C., the ice bath was replaced with a cold-water bath and the reaction mixture was stirred at 15-16° C. for 18 h. HPLC analysis showed 94% of cyanuric chloride conversion to 2-chloro-4,6,-bis(2,4-dimethylphenyl)-1,3,5-triazine and 2,4,6-tris(2,4-dimethylphenyl)-1,3,5-triazine in a ratio of 86:14.

Part B: Preparation of 2-(2,4-dihydroxyphenyl)-4,6-bis(2,4-dimethylphenyl)-1,3,5-triazine To the above reaction mixture was added 1.1 eq of resorcinol and the mixture was stirred at 85° C. for 2 h. HPLC analysis of the reaction mixture showed 84% of 2-(2,4-dihydroxyphenyl)-4,6-bis(2,4-dimethylphenyl)-1,3,5-triazine, 14% 2,4,6-tris(2,4-dimethylphenyl)-1,3,5-triazine, and 2% unreacted 2-chloro-4,6-bis(2,4-dimethylphenyl)-1,3,5-triazine.

Example 57

Preparation of 2-(2,4-dihydroxyphenyl)-4,6-bis(2,4-dimethylphenyl)-1,3,5-triazine Part A: Preparation of 2-chloro-4,6-bis(2,4-dimethylphenyl)-1,3,5-triazine using 0.5 eq of benzoyl chloride as promoter To a stirring mixture of 1 eq of cyanuric chloride and 3 eq of aluminum chloride in chlorobenzene at 1-2° C. was added 0.5 eq of benzoyl chloride over 10 min. After stilling for 10 min, 1.9 eq of m-xylene was added over 6 min. After stirring for 2 h at 0-1° C., the ice bath was replaced with a cold water bath and the reaction mixture was allowed to warm to 15-16° C. and stirred for 19 h. HPLC analysis showed 84% of cyanuric chloride conversion to 2-chloro-4,6-bis(2,4-dimethylphenyl)-1,3,5-triazine and 2,4,6-tris(2,4-dimethylphenyl)-1,3,5-triazine in a ratio of 86:14.

Part B: Preparation of 2-(2,4-dihydroxyphenyl)-4,6-bis(2,4-dimethylphenyl)-1,3,5-triazine To the above reaction mixture was added 1.1 eq of resorcinol and the mixture was stirred at 85° C. for 2 h. HPLC analysis of the reaction mixture showed 80% 2-(2,4-dihydroxyphenyl)-4,6-bis(2,4-dimethylphenyl)-1,3,5-triazine and 20% 2,4,6-tris(2,4-dimethylphenyl)-1,3,5-triazine.

Example 58

Preparation of 2-chloro-4,6-bis(2,4-dimethylphenyl)-1,3,5-triazine using 0.5 eq of propanesulfonyl chloride as promoter To a stirring mixture of 1 eq of cyanuric chloride and 3 eq of aluminum chloride in chlorobenzene at 0-1° C. was added 0.5 eq of propanesulfonyl chloride over 10 min. An immediate reaction with aluminum chloride was observed during the addition. After stirring for 10 min at 1-2° C., 1.9 eq of m-xylene was added over 6 min. After stirring for 2 h at 0-2° C., the ice bath was replaced with a cold water bath, the reaction was allowed to warm to 16-18° C. and was stirred for 20 h. HPLC analysis showed 92% of cyanuric chloride conversion to 2-chloro-4,6-bis(2,4-dimethylphenyl)-1,3,5-triazine and 2,4,6-tris(2,4-dimethylphenyl)-1,3,5-triazine in a ratio of 90:10.

Example 59

Preparation of 2-chloro-4,6-bis(2,4-dimethylphenyl)-1,3,5-triazine using 0.5 eq of p-toluenesulfonyl chloride as promoter To a stirring mixture of 1 eq of cyanuric chloride and 3 eq of aluminum chloride in chlorobenzene at 0-2° C. was added 0.5 eq of p-toluenensulfonyl chloride over 10 min. After stirring for 10 min, 1.9 eq of m-xylene was added over 6 min. After stirring at 0-1° C., the ice bath was replaced with a cold water bath, the reaction mixture was allowed to warm to 16-17° C. and was stirred for 21 h. The water bath was removed and the temperature was allowed to warm to 23° C. HPLC analysis showed the conversion of cyanuric chloride to 2-chloro-4,6-bis(2,4-dimethylphenyl)-1,3,5-triazine and 2,4,6-tris(2,4-dimethylphenyl)-1,3,5-triazine in a ratio of 79:21.

Example 60

Preparation of 2-chloro-4,6-bis(2,4-dimethylphenyl)-1,3,5-triazine using 0.5 eq of acetic anhydride as promoter To a stirring mixture of 1 eq of cyanuric chloride and 3 eq of aluminum chloride in chlorobenzene at 1-2° C. was added a solution of 0.5 eq of acetic anhydride in chlorobenzene over 10 min. An immediate reaction with aluminum chloride (exotherm) was observed during addition. After stirring for 10 min, 1.9 eq of m-xylene was added over 6 min. After stirring at 0-1° C. for 2 h, the ice bath was replaced with a cold water bath, the reaction mixture was allowed to warm to 16° C. and was stirred for 19 h. HPLC analysis showed the complete conversion of m-xylene, but only 72% conversion of cyanuric chloride to 2-chloro-4,6-bis(2,4-dimethylphenyl)-1,3,5-triazine and 2,4,6-tris(2,4-dimethylphenyl)-1,3,5-triazine in a ratio of 84:16.

Example 61

Preparation of 2-(2,4-dihydroxyphenyl)-4,6-bisphenyl-1,3,5-triazine

Part A: Preparation of 2-chloro-4,6-bisphenyl-1,3,5-triazine using concentrated HCl as a Reaction Promoter To a stirring mixture of 1 eq of cyanuric chloride and 3 eq of aluminum chloride in o-dichlorobenzene at ice bath temperature was added concentrated HCl (13 wt % based on cyanuric chloride). After 10 minutes, 1.95 eq of benzene was added and the reaction mixture stirred at ice bath temperature for 10 minutes. The cooling bath was removed, the reaction was allowed to warm to room temperature, and stirred. After 26 h at room temperature, an HPLC analysis indicated about 86% cyanuric chloride conversion to 2-chloro-2,6-bisphenyl-1,3,5-triazine. The stirring was continued for 24 h at room temperature. The HPLC analysis showed the cyanuric chloride conversion to 92% with >96% being 2-chloro-4,6-bisphenyl-1,3,5-triazine and less than 2% of 2,4,6-trisphenyl-1,3,5-triazine. The result was confirmed by LCMS Part B: Preparation of 2-(2,4-dihydroxyphenyl)-4,6-bisphenyl-1,3,5-triazine To the above reaction mixture was added 1.1 eq of resorcinol and the mixture was heated to 80° C. Within 2 h, HPLC analysis indicated about 80% of 2-chloro-4,6-bisphenyl-1,3, 5-triazine conversion to 2-(2,4-dihydroxyphenyl)-4,6-bisphenyl-1,3,5-triazine Comparative Example 61

Preparation of 2-chloro-4,6-bisphenyl-1,3,5-triazine without concentrated HCl

To a stirring mixture of 1 eq of cyanuric chloride and 3 eq of aluminum chloride in o-dichlorobenzene at ice bath temperature was added 1.95 eq of benzene and the reaction mixture was stirred at ice bath temperature for 10 minutes. The cooling bath was removed, the reaction mixture was allowed to warm to room temperature, and stirred. After about 26 h, an HPLC analysis indicated almost no cyanuric chloride conversion and no presence of 2-chloro-4,6-bisphenyl-1,3,5-triazine. The stirring was continued for an additional 24 h at room temperature. An HPLC analysis showed almost no cyanuric chloride conversion and no 2-chloro-4,6-bisphenyl-1,3,5-triazine.

Example 62

Preparation of 2-(2,4-dihydroxyphenyl)-4,6-bis(4-methylphenyl)-1,3,5-triazine

Part A: Preparation of 2-chloro-4,6-bis(4-methylphenyl)-1,3,5-triazine using concentrated HCl To a stirring mixture of 1 eq of cyanuric chloride and 3 eq of aluminum chloride in o-dichlorobenzene at ice bath temperature was added concentrated HCl (13 wt % based on cyanuric chloride). After 10 minutes, 1.9 eq of toluene was added and the reaction mixture was stirred at ice bath temperature for 30 minutes. The cooling bath was removed, the reaction mixture was allowed to warm to room temperature, and stirred for 21 h. HPLC analysis indicated about 95% cyanuric chloride conversion to 2-chloro-4,6-bis(4-methylphenyl)-1,3,5-triazine and the isomer 2-chloro-4-(4-methylphenyl)-6-(2-methylphenyl)-1,3,5-triazine Part B: Preparation of 2-(2,4-dihydroxyphenyl)-4,6-bis(4-methylphenyl)-1,3,5-triazine To the above reaction mixture was added 1.1 eq of resorcinol and the mixture was heated to 80° C. Within 3 h, an HPLC analysis indicated 2-chloro-4,6-bis(4-methylphenyl)-1,3,5-triazine had converted to 2-(2,4-dihydroxyphenyl)-4,6-bis(4-methylphenyl)-,1,3,5-triazine. HPLC analysis of the crude product showed 78% of 2-(2,4-dihydroxyphenyl)-4,6-bis(4-methylphenyl)-1,3,5-triazine, 11% of the isomer with probable structure of 2-(2,4-dihydroxyphenyl)-4-(4-methylphenyl)-6-(2-methylphenyl)-1,3,5-triazine Comparative Example 62

Preparation of 2-chloro-4,6 bis(4-methylphenyl-1,3,5-triazine without concentrated HCl To a stirring mixture of 1 eq of cyanuric chloride and 3 eq of aluminum chloride in o-dichlorobenzene at ice bath temperature was added 1.9 eq of toluene and the reaction mixture was stirred at ice bath temperature for 10 minutes. The cooling bath was removed, the reaction mixture was allowed to warm to room temperature. After about 2 h, an HPLC analysis indicated no reaction of cyanuric chloride. The stirring was continued for about 20 h at room temperature. HPLC analysis showed almost no reaction of cyanuric chloride and the absence of 2-chloro-4,6-bis(4-methylphenyl)-1,3,5-triazine Example 63

Preparation of 2-(2,4-dihydroxyphenyl)-4,6-bis(3,4-dimethylphenyl)-1,3,5-triazine Part A: Preparation of 2-chloro-4,6-bis(3,4-dimethylphenyl)-1,3,5-triazine using concentrated HCl To a stirring mixture of 1 eq of cyanuric chloride and 3 eq of aluminum chloride in o-dichlorobenzene at ice bath temperature was added concentrated HCl (13 wt % based on cyanuric chloride). After 30 minutes, the reaction was further cooled to about −5° C. and 1.9 eq of xylene was added. The reaction mixture was stirred at about 0° C. for 2 h, and then at room temperature for 4 h. HPLC analysis indicated >95% cyanuric chloride conversion to 82% 2-chloro-4,6-bis(3,4-dimethylphenyl)-1,3,5-triazine and 6% of its isomer.

Part B: Preparation of 2-(2,4-dihydroxyphenyl)-4,6-bis(3,4-dimethylphenyl)-1,3,5-triazine To the above reaction mixture was added 1.1 eq of resorcinol and the mixture was heated to 80° C. Within 2 h, an HPLC analysis indicated 2-chloro-4,6-bis(3,4-dimethylphenyl)-1,3,5-triazine and its isomer had completely reacted to form 83% of 2-(2,4-dihydroxyphenyl)-4,6-bis(3,4-dimethylphenyl)-1,3,5-triazine and 6% of its isomer.

Comparative Example 63

Preparation of 2-chloro-4,6-bis(3,4-methylphenyl)-1,3,5-triazine without concentrated HCl To a stirring mixture of 1 eq of cyanuric chloride and 3 eq of aluminum chloride in o-dichlorobenzene at ice bath temperature was added 1.9 eq of o-xylene and the reaction mixture was stirred at ice bath temperature for 1 h. The cooling bath was removed and the reaction mixture was allowed to warm to room temperature. After about 2 h, an HPLC analysis indicated no reaction of cyanuric chloride. The stirring was continued for about 20 h at room temperature. HPLC analysis showed no significant conversion of cyanuric chloride and the absence of 2-chloro-4,6-bis(3,4-methylphenyl)-1,3,5-triazine Example 64

Preparation of 2-(2,4-dihydroxyphenyl)-4,6-bis(4-biphenyl)-1,3,5-triazine

Part A: Preparation of 2-chloro-4,6-bis(4-biphenyl)-1,3,5-triazine using concentrated HCl To a stirring mixture of 1 eq of cyanuric chloride and 3 eq of aluminum chloride in o-dichlorobenzene at ice bath temperature was added concentrated HCl (13 wt % based on cyanuric chloride). After 10 minutes, 2 eq of biphenyl was added and the reaction was stirred at ice bath temperature for 1 h. HPLC analysis indicated 88% cyanuric chloride conversion to 2-chloro-4,6-bis(4-biphenyl)-1,3,5-triazine as the major product. The cooling bath was removed, the reaction mixture was allowed to warm to room temperature, and stirred. HPLC analysis after 3 h at room temperature indicated about 93% cyanuric chloride to 2-chloro-4,6-bis(4-biphenyl) as the major product and confirmed by MS.

Part B: Preparation of 2-(2,4-dihydroxyphenyl)-4,6-bis 4-biphenyl)-1,3,5-triazine To the above reaction mixture was added 1.1 eq of resorcinol and the mixture was heated to 85° C. for 2 h. HPLC and MS analysis indicated the formation of 2-(2,4-dihydroxyphenyl)-4,6-bis(4-biphenyl)-1,3,5-triazine.

Comparative Example 64

Preparation of 2-chloro-4,6-bis(4-biphenyl)-1,3,5-triazine without concentrated HCl To a stirring mixture of 1 eq of cyanuric chloride and 3 eq of aluminum chloride in o-dichlorobenzene at ice bath temperature was added 2 eq of biphenyl and the reaction mixture was stirred at ice bath temperature for 1 h. HPLC analysis indicated almost no cyanuric chloride conversion and the absence of 2-chloro-4,6-bis(4-biphenyl)-1,3,5-triazine. The cooling bath was removed and the reaction mixture was allowed to warm to room temperature. After about 3 h, an HPLC analysis indicated no reaction of cyanuric chloride and no formation of 2-chloro-4,6-bis(4-biphenyl)-1,3,5-triazine.

Example 65

Preparation of 2-(2,4-dihydroxyphenyl)-4,6-bis(4-tert-butylphenyl)-1,3,5-triazine Part A: Preparation of 2-chloro-4,6-bis(4-tert-butylphenyl)-1,3,5-triazine using concentrated HCl To a stirring mixture of 1 eq of cyanuric chloride and 3 eq of aluminum chloride in o-dichlorobenzene at ice bath temperature was added concentrated HCl (13 wt % based on cyanuric chloride). After 10 minutes, 1.95 eq of tert-butylbenzene was added and the reaction was stirred at ice bath temperature for 10 minutes. The cooling bath was removed, the reaction mixture was allowed to warm to room temperature, and stirred. After 2 h, HPLC analysis indicated 62% cyanuric chloride conversion to 2-chloro-4,6-bis(4-tert-butylphenyl)-1,3,5-triazine as the major product (>78%). The reaction mixture was stirred at room temperature for an additional 24 h HPLC analysis showed 83% cyanuric chloride conversion to 2-chloro-4,6-bis(4-tert-butylphenyl)-1,3,5-triazine as the major product (>72%), with the isomer.

Part B: Preparation of 2-(2,4-dihydroxyphenyl)-4,6-bis(4-tert-butylphenyl)-1,3,5-triazine To the above reaction mixture was added 1.1 eq of resorcinol and the mixture was heated to 80° C. for 2 h. HPLC analysis indicated 63% formation of 2-(2,4-dihydroxyphenyl)-4,6-bis(4-tert-butylphenyl)-1,3,5-triazine.

Comparative Example 65

Preparation of 2-chloro-4,6-bis(4-tert-butylphenyl)-1,3,5-triazine without concentrated HCl To a stirring mixture of 1 eq of cyanuric chloride and 3 eq of aluminum chloride in o-dichlorobenzene at ice bath temperature was added 1.95 eq of tert-butylbenzene. The reaction mixture was stirred at ice bath temperature for 10 minutes. The cooling bath was removed, the reaction mixture was allowed to warm to room temperature, and stirred. After about 2 h, an HPLC analysis indicated no reaction of cyanuric chloride and no 2-chloro-4,6-(4-tert-butylphenyl)-1,3,5-triazine formation. The stirring was continued for about 24 h at room temperature. HPLC analysis showed no 2-chloro-4,6-bis(4-tert-butylphenyl)-1,3,5-triazine formation.

Example 66

Preparation of 2-(2,4-dihydroxy-5-hexylphenyl)-4,6-bis(4-tert-butylphenyl)-1,3,5-triazine Part A: Preparation of 2-chloro-4,6-bis(4-tert-butylphenyl)-1,3,5-triazine using concentrated HCl 2-Chloro-4,6-bis(4-tert-butylphenyl)-1,3,5-triazine was prepared essentially following the procedure described in example 67.

Part B: Preparation of 2-(2,4-dihydroxy-5-hexylphenyl)-4,6-bis(4-tert-butylphenyl)-1,3,5-triazine To the above reaction mixture was added 1.1 eq of 4-hexylresorcinol and the mixture was heated to 80° C. for 3 h. HPLC analysis indicated conversion of 2-chloro-4,6-bis(4-tert-butylphenyl)-1,3,5-triazine to 2-(2,4-dihydroxy-5-hexylphenyl)-4,6-bis(4-tert-butylphenyl)-1,3,5-triazine as the major product.

Example 67

Preparation of 2-(2-hydroxy-4-octyloxyphenyl)-4,6-bis(2,4-dimethylphenyl)-1,3,5-triazine Part A: Preparation of 2-chloro-4,6-bis(2,4-dimethylphenyl)-1,3,5-triazine 2-Chloro-4,6-bis(2,4-dimethylphenyl)-1,3,5-triazine was prepared by allowing to react 1 eq of cyanuric chloride with 1.9 eq of m-xylene in the presence of 3 eq of aluminum chloride and concentrated HCl in chlorobenzene as discussed above.

Part B: Preparation of 2-(2-hydroxy-4-octyloxyphenyl)-4,6-bis(2,4-dimethylphenyl)-1,3,5-triazine To the above reaction mixture was added 1.1 eq of resorcinol monooctyl ether and the mixture was stirred at room temperature for about 20 h. ILC analysis indicated formation of 2-(2-hydroxy-4-octyloxyphenyl)-4,6-bis(2,4-dimethylphenyl)-1,3,5-triazine as the major product by a direct comparison with a commercial sample of 2-(2-hydroxy-4-octyloxyphenyl)-4,6-bis(2,4-dimethylphenyl)-1,3,5-triazine.

Example 68

Preparation of 2-(2,4-dihydroxyphenyl)-4,6-bis(2,4-dimethylphenyl)-1,3,5-triazine Part A: Preparation of 2-chloro-4,6-bis(2,4-dimethylphenyl)-1,3,5-triazine; Simultaneous addition of cyanuric chloride and m-xylene to reaction facilitator prepared from aluminum chloride and concentrated HCl To a stirring mixture of 3 eq. of aluminum chloride in chlorobenzene at 0° C. to 5° C. was added concentrated HCl (6 wt % based on aluminum chloride), and the reaction mixture was stirred for 10 minutes to form the reaction facilitator. To the mixture was added a solution of 1 eq of cyanuric chloride and 1.9 eq of m-xylene in chlorobenzene at 0° C. to 5° C. and the reaction was stirred for 10 minutes. HPLC analysis indicated 95% cyanuric chloride conversion to 2-chloro-4,6-bis(2,4-dimethylphenyl)-1,3,5-triazine (99%). The reaction mixture was allowed to stir at 0° C. to 5° C. for 2 h. HPLC analysis showed 99% cyanuric chloride conversion to 2-chloro-4,6-bis(2,4-dimethylphenyl)-1,3,5-triazine (98%).

Part B: Preparation of 2-(2,4-dihydroxyphenyl)-4,6-bis(2,4-dimethylphenyl)-1,3,5-triazine To the above reaction mixture was added 1.1 eq of resorcinol and the mixture was heated to 80° C. for 2 h. HPLC analysis indicated 95% of 2-(2,4-dihyroxyphenyl)-4,6-bis(2,4-dimethylphenyl)-1,3,5-triazine.

Example 69

Preparation of 2-chloro-4,6-bis(2,4-dimethylphenyl-1,3,5-triazine in benzene as solvent and concentrated HCl To a stirring mixture of 1 eq of cyanuric chloride and 3 eq of aluminum chloride in benzene at 7° C. was added concentrated HCl (13% wt based on cyanuric chloride), and the mixture was stirred for 10 minutes. To the reaction mixture was added 1.9 eq of m-xylene and the reaction mixture was stirred at 0° C. for 30-35 minutes. The cooling bath was removed, the reaction mixture was allowed to warm to room temperature, and stirred for 3 h. HPLC analysis indicated >97% cyanuric chloride conversion to 2-chloro-4,6-(2,4-dimethylphenyl)-1,3,5-triazine (85%).

Example 70

Preparation of 2-(2,4-dihydroxy-6-methylphenyl)-4,6-bis(2,4-dimethylphenyl)-1,3,5-triazine Part A: Preparation of 2-chloro-4,6-bis(2,4-dimethylphenyl)-1,3,5-triazine complex with reaction facilitator prepared from aluminum chloride and concentrated HCl To a stirring mixture of 1 eq of isolated 2-chloro-4,6-bis(2,4-dimethylphenyl)-1,3,5-triazine and 3 eq of aluminum chloride in o-dichlorobenzene was added concentrated HCl (5.9 wt % based on aluminum chloride). After stirring for about 5-6 h at room temperature, the reaction turned orange-red, indicative of a new complex formed between the reaction facilitator, consisting of aluminum chloride and concentrated HCl, and 2-chloro-4,6-bis(2,4-dimethylphenyl)-1,3,5-triazine.

Part B. Preparation of 2-(2,4-dihydroxy-6-methylphenyl)-4,6-bis(2,4-dimethylphenyl)-1,3,5-triazine The above complex mixture was heated to about 60° C. To the mixture was added 1 eq of orcinol (5-methylresorcinol), and the reaction mixture was heated to 80° C. to 85° C. for 8 h. HPLC analysis indicated almost complete conversion of 2-chloro-4,6-bis(2,4-dimethylphenyl)-1,3,5-triazine leading to the formation of 2-(2,4-dihyroxy-6-methylphenyl)-4,6-bis(2,4-dimethylphenyl)-1,3,5-triazine.

Comparative Example 70

Preparation of 2-chloro-4,6-bis(2,4-dimethylphenyl)-1,3,5-triazine complex with aluminum chloride without concentrated HCl A mixture of 1 eq of isolated 2-chloro-4,6-bis(2,4-dimethylphenyl)-1,3,5-triazine and 3 eq of aluminum chloride in o-dichlorobenzene was stirred at room temperature for about 5-6 h. The reaction mixture turned slightly yellow and was not orange-red as in the preceding example, indicative of a lack of the new complex formation from 2-chloro-4,6-bis(2,4-dimethylphenyl)-1,3,5-triazine.

Example 71

Preparation of reaction facilitator from aluminum chloride and concentrated HCl

To a stirring mixture of 3 eq of aluminum chloride in o-dichlorobenzene was added concentrated HCl (6 wt % based on aluminum chloride). The reaction mixture was stirred at room temperature. The formation of a new off-white mixture of the reaction facilitator was observed, which did not change its color even after stirring at room temperature for 2 h.

Example 72

Preparation of 2,4,6-trichloro-1,3,5-triazine (cyanuric chloride) complex with reaction facilitator prepared from aluminum chloride and concentrated HCl To a stirring mixture of 1 eq of cyanuric chloride and 3 eq of aluminum chloride in o-dichlorobenzene was added concentrated HCl (13 wt % based on cyanuric chloride). The reaction mixture turned brownish-red after 30 minutes of stirring at room temperature. The reaction became dark brown after an additional 1 h of stirring at room temperature. The color of the reaction mixture indicated the formation of a new complex between cyanuric chloride and the reaction facilitator prepared from aluminum chloride and concentrated HCl.

Comparative Example 72

Preparation of 2,4,6-trichloro-1,3,5-triazine (cyanuric chloride) complex with reaction facilitator prepared from aluminum chloride without concentrated HCl A mixture of 1 eq of cyanuric chloride and 3 eq of aluminum chloride in o-dichlorobenzene was stirred at room temperature for 3 h. No change in color from original off-white was observed, indicating lack of a similar complex formation of cyanuric chloride as in the preceding example, where cyanuric chloride was treated with the reaction facilitator consisting of aluminum chloride and concentrated HCl.

Example 73

Preparation of 2-chloro-4,6-bis(2,4-dimethylphenyl)-1,3,5-triazine using Aliquat-336

To a stirring mixture of 1 eq of cyanuric chloride and 3 eq of aluminum chloride in benzene at about 0° C. was added Aliquat-336 (tricaprylylmethylammonium chloride) (50 wt % based on aluminum chloride). A reaction with aluminum chloride was observed with temperature increase. The reaction mixture was stirred at room temperature for 30 minutes, leading to the formation of a clear orange-red solution. To the resulting complex of cyanuric chloride with reaction facilitator was added 1.9 eq of m-xylene and the reaction mixture was stirred at room temperature for 1 h. HPLC analysis indicated almost 90% cyanuric chloride conversion to 2-chloro-4,6-(2,4-dimethylphenyl)-1,3,5-triazine as the major product and 2,4,6-tris(2,4-dimethylphenyl)-1,3,5-triazine as the minor product, formed in a ratio of 3:1.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A process for synthesizing a trisaryl triazine compound comprising reacting a cyanuric halide of Formula V:

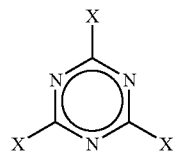

Formula V where each X is independently a halide such as fluorine, chlorine, bromine or iodine, with a compound of Formula II:

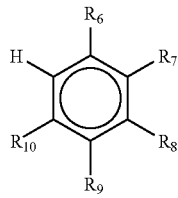

Formula II wherein $R_6$, $R_7$, $R_8$, $R_9$, and $R_{10}$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, $SO_2R$, $SO_3H$, $SO_3M$, wherein M is an alkali metal, R and $R^1$ are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, and optionally with either of $R_6$ and $R_7$, $R_7$ and $R_8$, $R_8$ and $R_9$, or $R_9$ and $R_{10}$, taken together being a part of a saturated or unsaturated fused carbocyclic ring optionally containing O, N, or S atoms in the ring, in the presence of at least one solvent and a reaction facilitator comprising at least one Lewis acid and at least one reaction promoter, for a sufficient time, at a suitable temperature and pressure to form the trisaryl triazine compound, with the proviso that the reaction promoter is different than the compound of Formula II.

2. The process according to claim 1, wherein the Lewis acid is present in an amount between about 0.5 to about 500 mol equivalents to the reaction promoter.

3. The process according to claim 1, wherein the Lewis acid is aluminum halide, boron halide, tin halide, zinc halide, lead halide, manganese halide, magnesium halide, copper halide, titanium halide, alkyl aluminum halide, gallium halide, iron halide, arsenic halide, antimony halide, or a mixture thereof.

4. The process according to claim 1, wherein the Lewis acid is aluminum chloride, aluminum bromide, boron trifluoride, tin chloride, zinc chloride, titanium tetrachloride, or a mixture thereof.

5. The process according to claim 1, wherein the reaction promoter is an acid, base, water, alcohol, aliphatic halide, halide salt, acid halide, halogen, alkene, alkyne, ester, anhydride, carbonate, urethane, carbonyl, epoxy, ether or acetal compound or a mixture thereof.

6. The process according to claim 1, wherein the solvent is selected from heptane, carbon disulfide, cyclohexane, chlorobenzene, dichlorobenzene, trichlorobenzene, bromobenzene, dibromobenzene, tribromobenzene, toluene, xylene, trimethylbenzene, nitrobenzene, dinitrobenzene, anisole, nitroalkanes, heptane, cyclohexane, benzene, nitrobenzene, dinitrobenzene, toluene, xylene, 1,1,2,2-tetrachloroethane, dichloromethane, dichloroethane, ether, dioxane, tetrahydro furan, benzonitriles, dimethylsulfoxide, tetramethylene sulfone, carbon disulfide, and benzene rings substituted with at least one halide including chlorobenzene, dichlorobenzene, trichlorobenzene, fluorobenzene, difluorobenzene, trifluorobenzene, bromobenzene, dibromobenzene, tribromobenzene, or mixtures thereof.

7. The process according to claim 1, further comprising forming the reaction facilitator before combining the mixture with the cyanuric halide of Formula V or the compound of Formula II.

8. The process according to claim 1, further comprising forming a mixture of the cyanuric halide of Formula V, the compound of Formula II, and a portion of the solvent before adding the reaction facilitator to the mixture.

9. The process according to claim 1, wherein the compound of Formula II is added between about 5 minutes to 15 hours and at a temperature between about −50° C. to about 150° C. and the reaction temperature is between about −50° C. to about 150° C.

10. The process according to claim 1, wherein the Lewis acid is mixed with the cyanuric halide of Formula V prior to adding the reaction promoter.

11. The process according to claim 1, wherein the Lewis acid is mixed with the compound of Formula II prior to adding the reaction promoter.

12. The process according to claim 1, wherein the reaction promoter is mixed with the compound of Formula V prior to adding the Lewis acid.

13. The process according to claim 1, wherein the reaction promoter is mixed with the compound of Formula II prior to adding the Lewis acid.

14. The process according to claim 2, wherein the Lewis acid is present in an amount of about 1 to about 10 mol equivalents to the cyanuric halide of Formula V.

15. The process according to claim 1, wherein the reaction promoter is present in an amount of about 0.01 to 5 mol equivalents to the cyanuric halide of Formula V.

16. The process according to claim 5, wherein the reaction promoter is a protic acid.

17. The process according to claim 16, wherein the protic acid contains at least one acidic functional group including $RCO_2H$, $RSO_3H$, $RSO_2H$, RSH, ROH, $RPO_3H$, $RPO_2H$, wherein R is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms.

18. The process according to claim 16, wherein the protic acid is HCl, HBr, HI, $HNO_3$, $HNO_2$, $H_2S$, $H_2SO_4$, $H_3PO_4$, $H_2CO_3$, acetic acid, formic acid, proprionic acid, butanoic acid, benzoic acid, phthalic acid, oxalic acid, malonic acid, succinic acid, glutaric acid, adipic acid, methanesulfonic acid, p-toluenesulfonic acid, or mixtures thereof.

19. The process according to claim 5, wherein the reaction promoter is water, acid, or a mixture thereof.

20. The process according to claim 5, wherein the reaction promoter is an aliphatic halide.

21. A process for synthesizing a trisaryl triazine compound comprising reacting a cyanuric halide of Formula V:

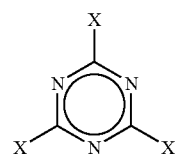

Formula V where each X is independently a halide such as fluorine, chlorine, bromine or iodine, with a compound of Formula II:

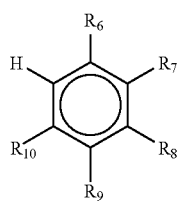

Formula II wherein $R_6$, $R_7$, $R_8$, $R_9$, and $R_{10}$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbon atoms, and optionally with either of $R_6$ and $R_7$, $R_7$ and $R_8$, $R_8$ and $R_9$, or $R_9$ and $R_{10}$, taken together being a part of a saturated or unsaturated fused carbocyclic ring optionally containing O, N, or S atoms in the ring, in the presence of a reaction facilitator comprising at least one Lewis acid and at least one reaction promoter, wherein the reaction promoter is present in an amount of about 0.01 to 5 mol equivalents to the cyanuric halide of Formula V, for a sufficient time, at a suitable temperature and pressure to form the trisaryl triazine compound, with the proviso that the reaction promoter is different than the compound of Formula II.

* * * * *

UNITED STATES PATENT AND TRADEMARK OFFICE
CERTIFICATE OF CORRECTION

PATENT NO.        : 7,485,723 B2                                          Page 1 of 1
APPLICATION NO. : 11/531932
DATED             : February 3, 2009
INVENTOR(S)       : Ram B. Gupta et al.

It is certified that error appears in the above-identified patent and that said Letters Patent is hereby corrected as shown below:

In Claim 1, Column 56, line 34, part of the sentence was omitted.

Insert --solvent and the-- in front of "compound of Formula II."

Signed and Sealed this

Thirty-first Day of March, 2009

JOHN DOLL
*Acting Director of the United States Patent and Trademark Office*